(12) United States Patent
Martin et al.

(10) Patent No.: US 10,004,491 B2
(45) Date of Patent: Jun. 26, 2018

(54) SUTURING INSTRUMENT WITH NEEDLE MOTION INDICATOR

(71) Applicant: Ethicon Endo-Surgery, LLC, Guaynabo, PR (US)

(72) Inventors: David T. Martin, Milford, OH (US); Andrew C. Deck, Dayton, OH (US); Daniel J. Mumaw, Liberty Township, OH (US); Mark J. Bookbinder, Blue Ash, OH (US); William J. White, West Chester, OH (US); Frederick E. Shelton, IV, Hillsboro, OH (US); Adam Hensel, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 190 days.

(21) Appl. No.: 14/739,235

(22) Filed: Jun. 15, 2015

(65) Prior Publication Data

US 2016/0361055 A1  Dec. 15, 2016

(51) Int. Cl.
*A61B 17/04* (2006.01)
*A61B 17/062* (2006.01)
(Continued)

(52) U.S. Cl.
CPC ........ *A61B 17/0469* (2013.01); *A61B 17/062* (2013.01); *A61B 17/0625* (2013.01);
(Continued)

(58) Field of Classification Search
CPC .......... A61B 17/0469; A61B 17/06133; A61B 17/062; A61B 17/0625;
(Continued)

(56) References Cited

U.S. PATENT DOCUMENTS 3,749,238 A * 7/1973 Taylor .............. A61B 17/06123
                                                206/227
3,815,843 A * 6/1974 Fortune .................. B23K 3/063
                                                242/137.1
(Continued)

FOREIGN PATENT DOCUMENTS

WO   WO 2010/031064 A1   3/2010
WO   WO 2010/127274 A1   11/2010
WO   WO 2014/147619 A1   9/2014

OTHER PUBLICATIONS

International Search Report and Written Opinion dated Jul. 29, 2016 for Application No. PCT/US2016/035390, 13 pgs.

*Primary Examiner* — Eric Rosen
*Assistant Examiner* — Son Dang
(74) *Attorney, Agent, or Firm* — Frost Brown Todd LLC

(57) ABSTRACT

A surgical instrument includes a body, a user input feature, an elongate shaft extending from the body along a longitudinal axis, and a needle applier coupled to the elongate shaft. The needle applier further includes a needle and a drive assembly coupled to the needle. The drive assembly is configured to rotate the needle about a rotation axis that is transverse to the longitudinal axis, in response to an actuation of the user input feature. The needle applier further includes a housing containing the needle and the drive assembly. The housing presents at least one indicator. The least one indicator is positioned to indicate at least one of a position of the needle relative to the housing, and a direction of rotation of the needle relative to the housing.

6 Claims, 20 Drawing Sheets

(51) Int. Cl.
*A61B 17/06* (2006.01)
*A61B 17/00* (2006.01)
*A61B 90/00* (2016.01)

(52) U.S. Cl.
CPC ............... *A61B 17/06133* (2013.01); *A61B 2017/0023* (2013.01); *A61B 2017/00473* (2013.01); *A61B 2017/00477* (2013.01); *A61B 2017/0479* (2013.01); *A61B 2017/0608* (2013.01); *A61B 2090/0811* (2016.02)

(58) Field of Classification Search
CPC .. A61B 2017/00473; A61B 2017/0608; A61B 2017/0023; A61B 2017/00477; A61B 2090/0811; A61B 2017/0479
See application file for complete search history.

(56) References Cited

U.S. PATENT DOCUMENTS

| | | | |
|---|---|---|---|
| 3,901,244 A * | 8/1975 | Schweizer | A61B 17/04 206/63.3 |
| 4,084,692 A * | 4/1978 | Bilweis | A61B 17/06123 206/403 |
| 4,890,615 A * | 1/1990 | Caspari | A61B 17/0469 606/139 |
| 5,131,534 A * | 7/1992 | Brown | A61B 17/06123 206/339 |
| 5,755,729 A * | 5/1998 | de la Torre | A61B 17/0469 112/169 |
| 5,911,829 A * | 6/1999 | Maksudian | A61B 17/06123 118/123 |
| 6,467,612 B1 * | 10/2002 | Rosenfeld | A61B 17/06123 206/63.3 |
| 7,022,085 B2 | 4/2006 | Cooke et al. | |
| 7,766,925 B2 * | 8/2010 | Stokes | A61B 1/00087 606/139 |
| 8,123,764 B2 * | 2/2012 | Meade | A61B 17/0469 606/145 |
| 8,333,776 B2 | 12/2012 | Cheng et al. | |
| 8,568,428 B2 | 10/2013 | McClurg et al. | |
| 8,679,136 B2 * | 3/2014 | Mitelberg | A61B 1/00087 606/144 |
| 8,702,732 B2 | 4/2014 | Woodard, Jr. et al. | |
| 9,168,037 B2 | 10/2015 | Woodard, Jr. et al. | |
| 9,357,998 B2 | 6/2016 | Martin et al. | |
| 9,375,212 B2 | 6/2016 | Martin et al. | |
| 9,474,522 B2 * | 10/2016 | Deck | A61B 17/0469 |
| 9,486,126 B2 * | 11/2016 | West | A61B 1/018 |
| 2003/0204195 A1 * | 10/2003 | Keane | A61B 17/0401 606/146 |
| 2005/0085851 A1 * | 4/2005 | Fiehler | A61B 17/0057 606/213 |
| 2006/0282098 A1 * | 12/2006 | Shelton, IV | A61B 1/00087 606/144 |
| 2009/0210006 A1 * | 8/2009 | Cohen | A61B 17/06166 606/232 |
| 2011/0046645 A1 * | 2/2011 | McClurg | A61B 17/0469 606/145 |
| 2013/0035631 A1 * | 2/2013 | Spilgies | A61M 37/0069 604/57 |
| 2013/0296889 A1 | 11/2013 | Tong et al. | |
| 2014/0039527 A1 * | 2/2014 | Avelar | A61B 17/06166 606/144 |
| 2014/0166514 A1 * | 6/2014 | Martin | A61B 17/0483 206/365 |
| 2015/0133967 A1 * | 5/2015 | Martin | A61B 17/0482 606/144 |

* cited by examiner

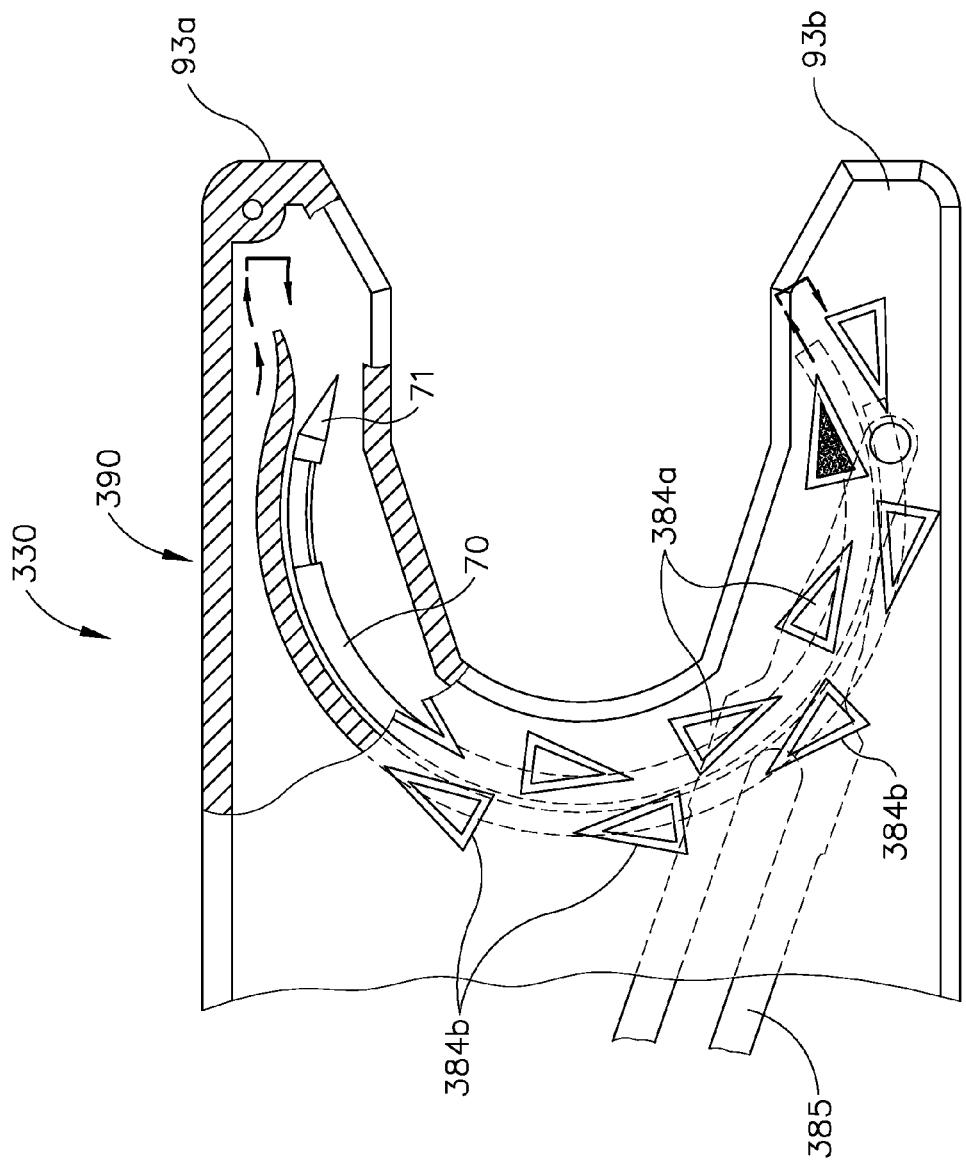

US 10,004,491 B2

SUTURING INSTRUMENT WITH NEEDLE MOTION INDICATOR

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laparoscopic Suture Device with Asynchronous In-Line Needle Movement," published Dec. 22, 2011, now U.S. Pat. No. 9,168,037, issued Oct. 27, 2015 the disclosure of which is incorporated by reference herein; U.S. Pub. No. 2014/0171970, entitled "Circular Needle Applier with Articulating and Rotating Shaft," published Jun. 19, 2014, now U.S. Pat. No. 9,357,998, issued Jun. 7, 2016 the disclosure of which is incorporated by reference herein; and U.S. patent application Ser. No. 14/297,993, entitled "Jawed Receiver for Needle Cartridge," filed Jun. 6, 2014, now U.S. Pat. No. 9,474,522, issued Oct. 25, 2016 the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts a top plan view of a distal end of another exemplary alternative cartridge configured for receipt in the cartridge receiving assembly of FIG. 2A, with a portion of the distal end shown in cross-section;

Figure 1:
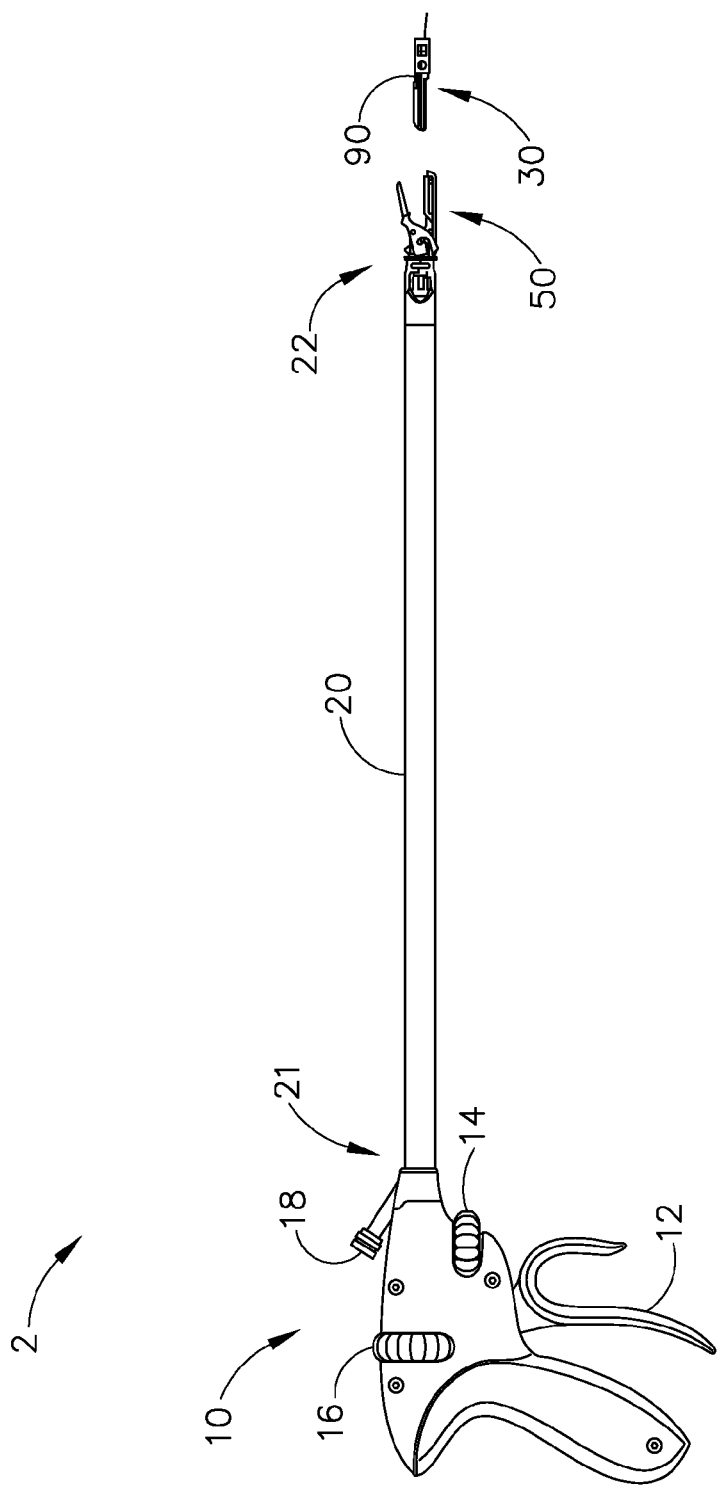
FIG. 1 depicts a side view of an exemplary surgical suturing instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Surgical Suturing Instrument

FIG. 1 illustrates an example of a surgical suturing instrument (2). Instrument (2) comprises a handle assembly (10), an elongate shaft (20), and a cartridge receiving assembly (50), which is operable to receive a needle applier cartridge (30). Shaft (20) has a proximal end (21), a distal end (22), and a longitudinal axis extending therebetween. Handle assembly (10) is connected to the proximal end (21) of the shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to the distal end (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first input (12), shown here as a trigger that pivots between opened and closed positions, may be used to selectively actuate needle applier cartridge (30). The trigger may be spring biased to return the trigger to its open position. A second input (14), shown here as a rotary knob, may be used to selectively articulate shaft (20). A third input (16), shown here as a rotary knob, may be used to selectively rotate needle applier cartridge (30) about shaft (20). Of course, the number, type, configuration, and operation of inputs (12, 14, 16) may vary.

Figure 2A:
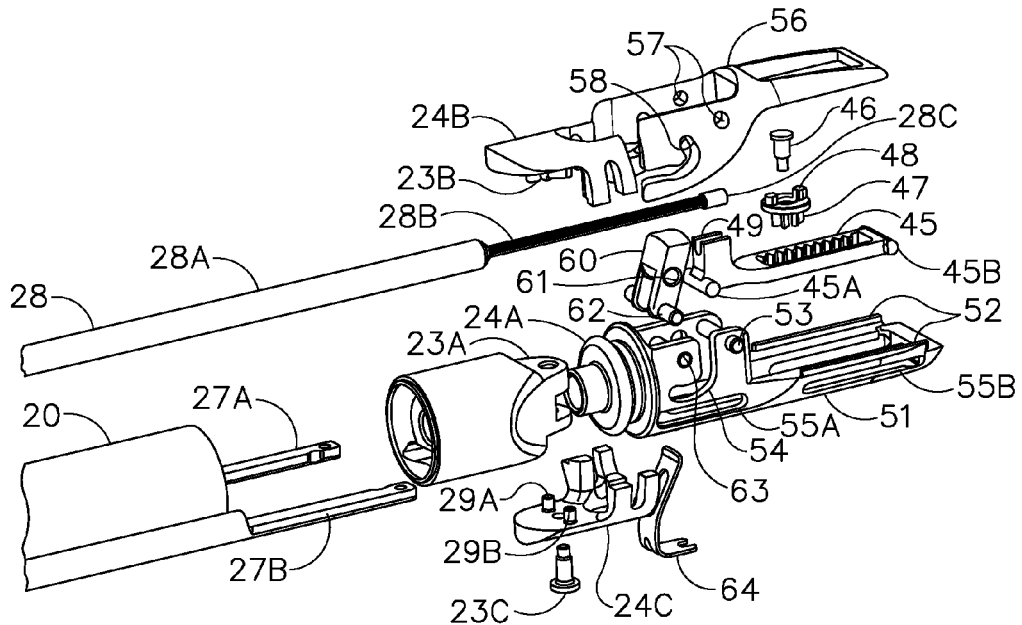
FIG. 2A depicts top perspective exploded view of a cartridge receiving assembly of the instrument of FIG. 1.
Figure 2B:
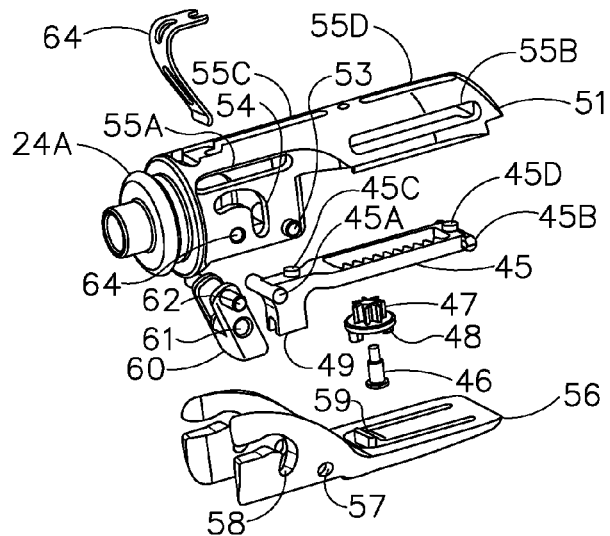
FIG. 2B depicts bottom perspective exploded view of the cartridge receiving assembly of FIG. 2A.

FIGS. 2A-2B illustrate exploded views of cartridge receiving assembly (50) of the present example. Distal end (22) of shaft (20) comprises an articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to second input (14) to opposingly push and pull rods (27A, 27B). In other words, second input (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by the pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first input (12) and to third input (16). Actuation of first input (12) will impart axial push and pull loads on drive rod (28) to longitudinally reciprocate rack (45) and thereby actuate needle applier cartridge (30). Actuation of third input (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
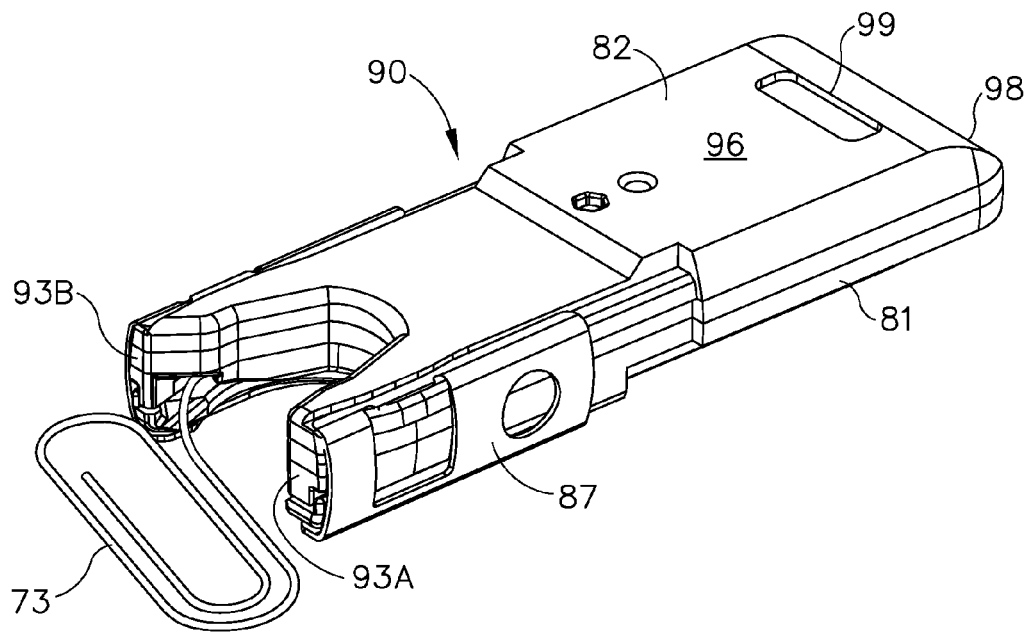
FIG. 3A depicts a top perspective view of an exemplary cartridge configured for receipt in the cartridge receiving assembly of FIG. 2A.
Figure 3B:
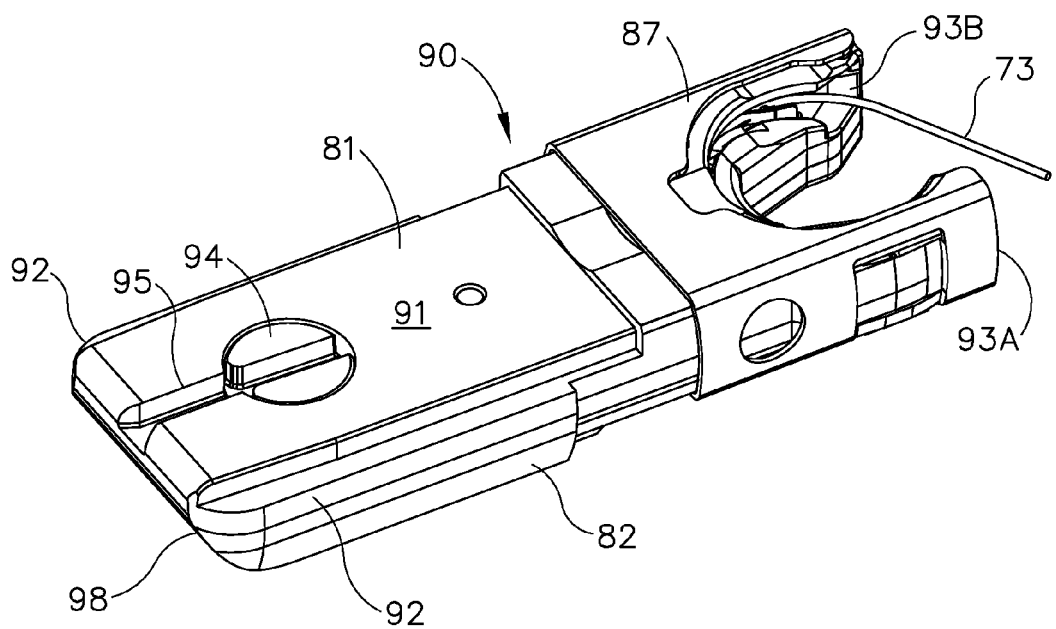
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
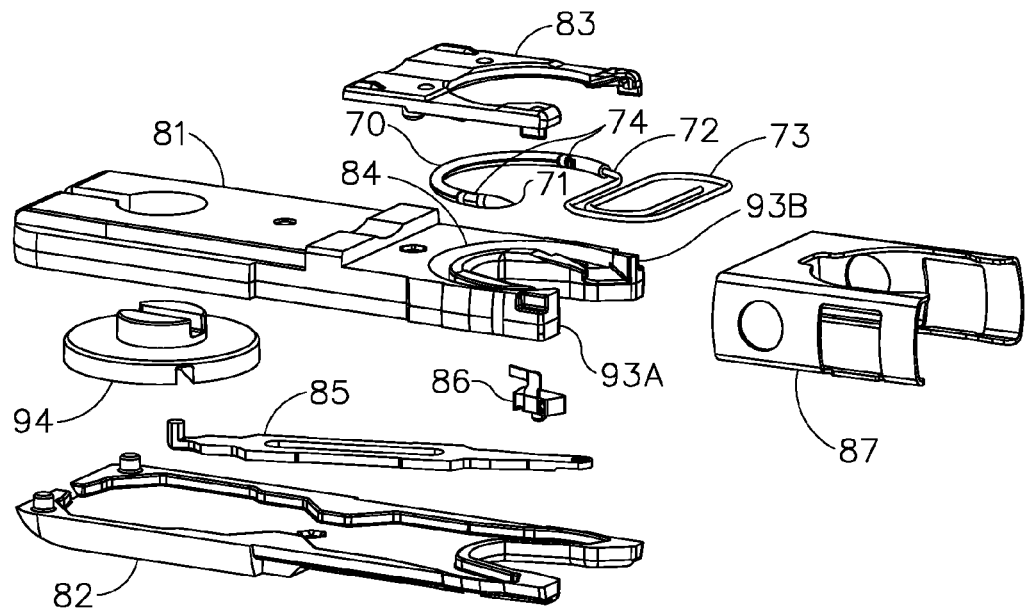
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from the trailing end (72). Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
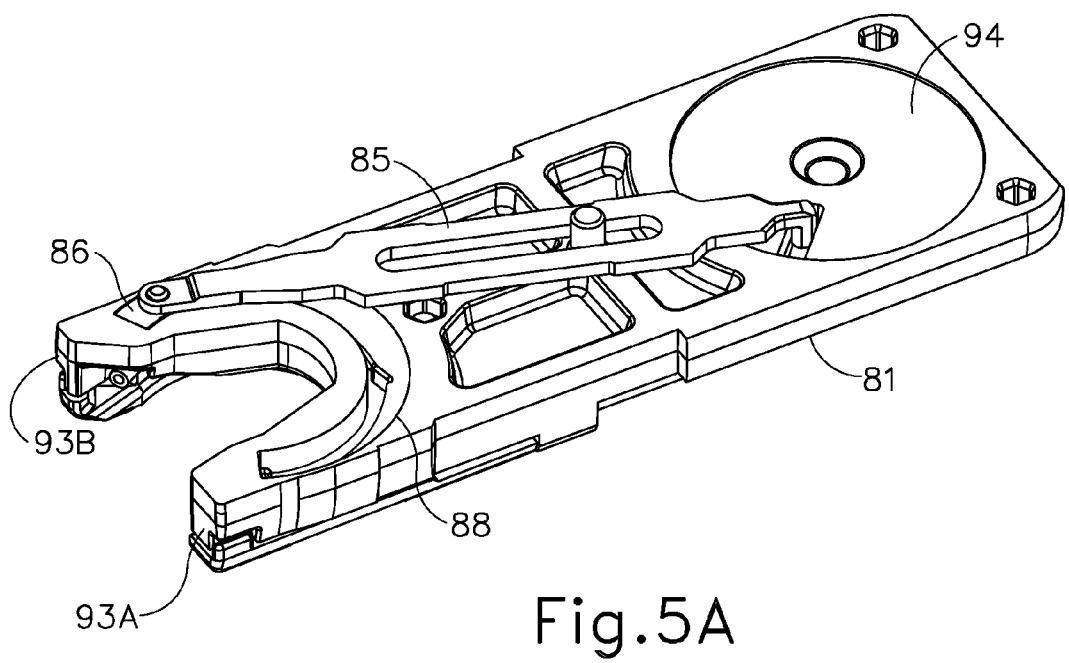
FIG. 5A depicts a perspective view of a drive assembly of the cartridge of FIG. 3A, with the drive assembly at one end of its stroke.
Figure 5B:
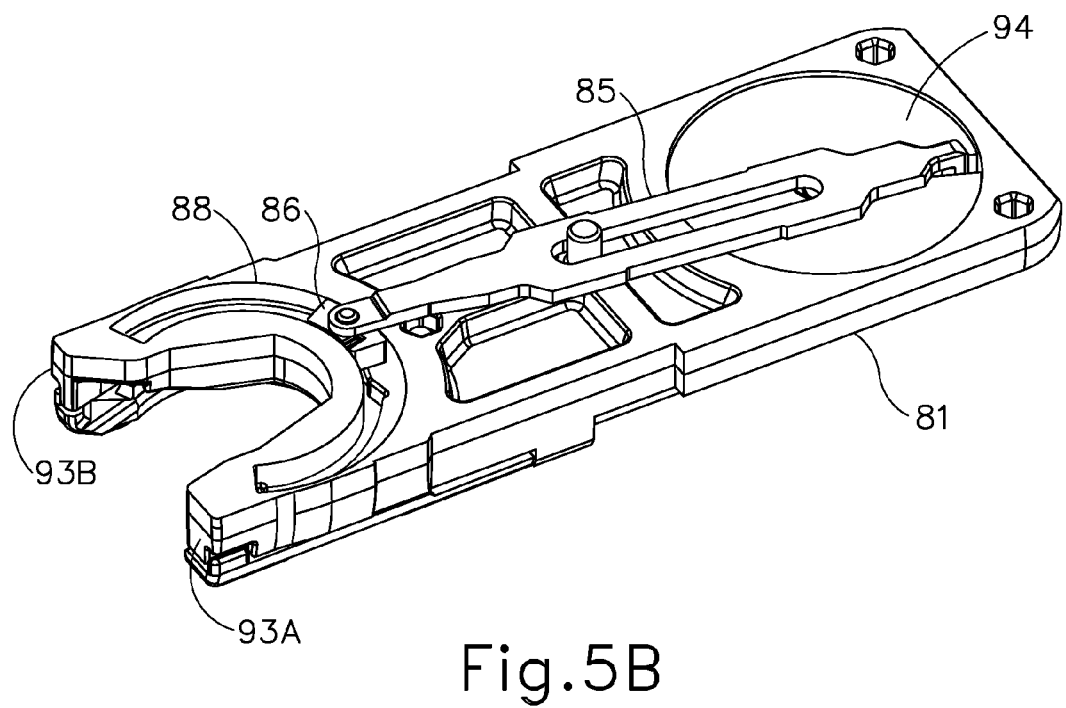
FIG. 5B depicts a perspective view of the drive assembly of FIG. 5A, with the drive assembly at mid-stroke.
Figure 5C:
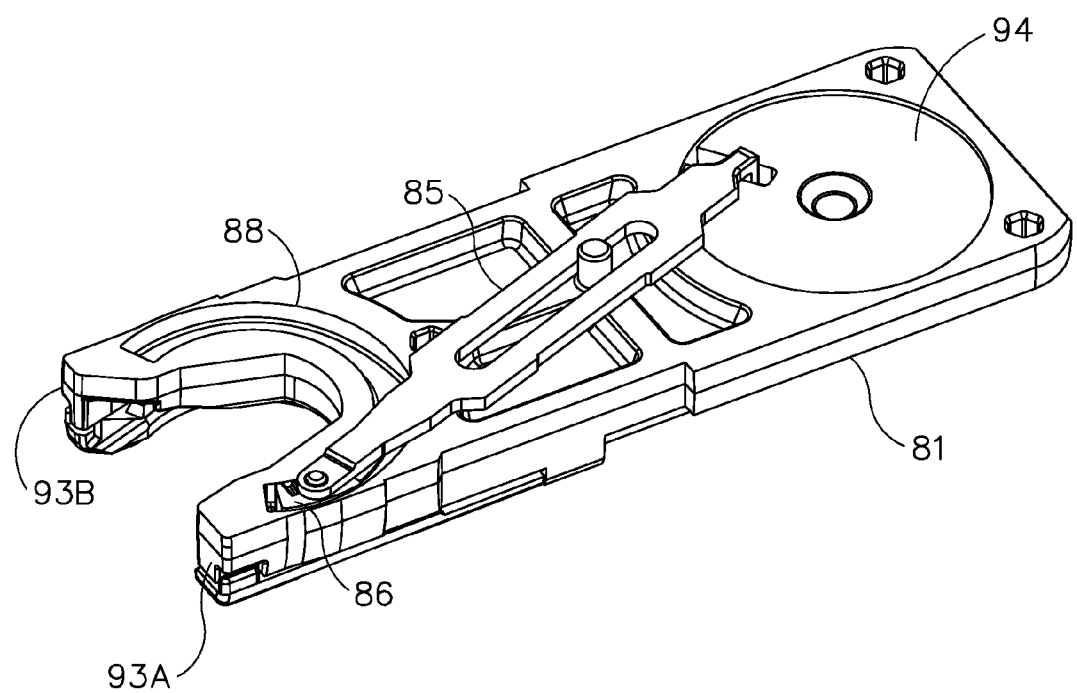
FIG. 5C depicts a perspective view of the drive assembly of FIG. 5A, with the drive assembly at the other end of its stroke.

FIGS. 5A-5C illustrate an example of a drive stroke of the drive assembly in cartridge body (90) for driving needle (70) in a circular, orbital path. However, it should be understood that needle (70) and suture (73) omitted from FIGS. 5B-5C. Needle driver (86) rides in a carrier track (88) and extends into needle track (84) to engage and drive needle (70). A link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
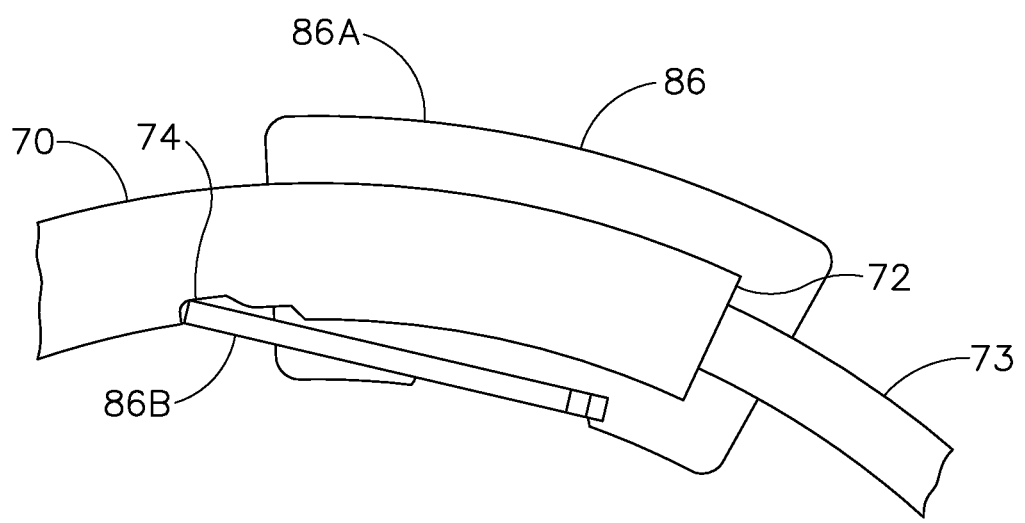
FIG. 6 depicts a partial plan view of a needle driver of the cartridge of FIG. 3A engaging a needle of the cartridge of FIG. 3A.
Figure 7:
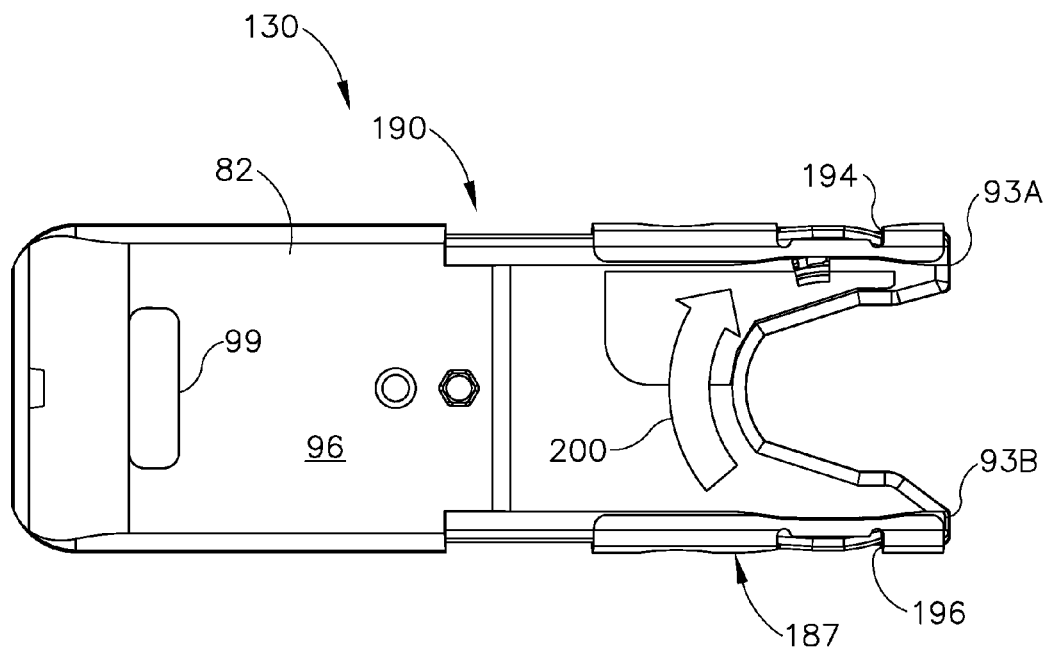
FIG. 7 depicts a top plan view of an exemplary alternative cartridge configured for receipt in the cartridge receiving assembly of FIG. 2A.
Figure 8:
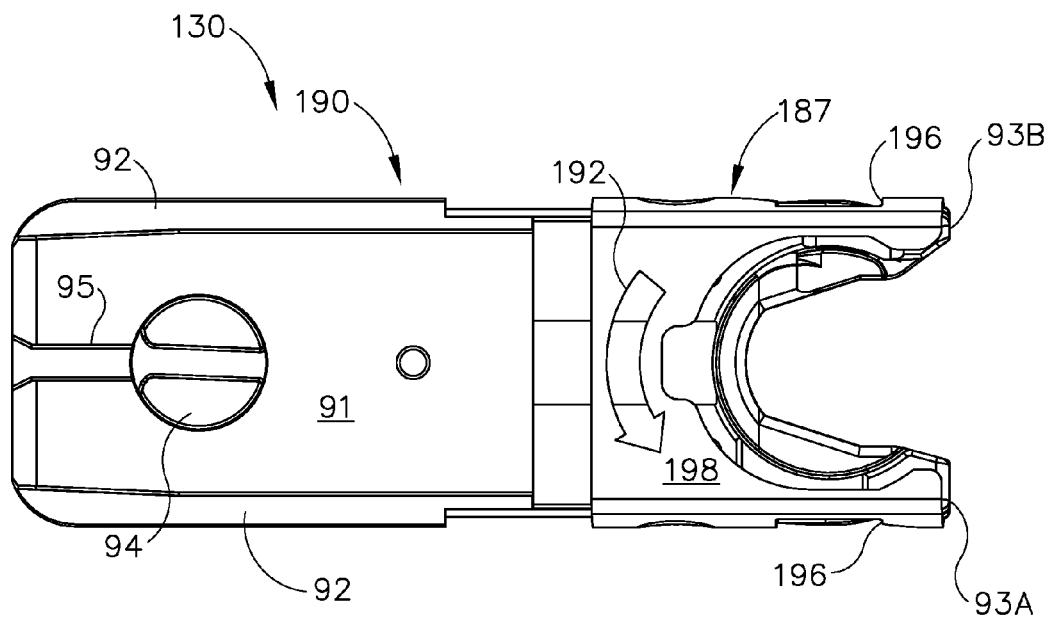
FIG. 8 depicts a bottom plan view of the cartridge of FIG. 7.
Figure 9:
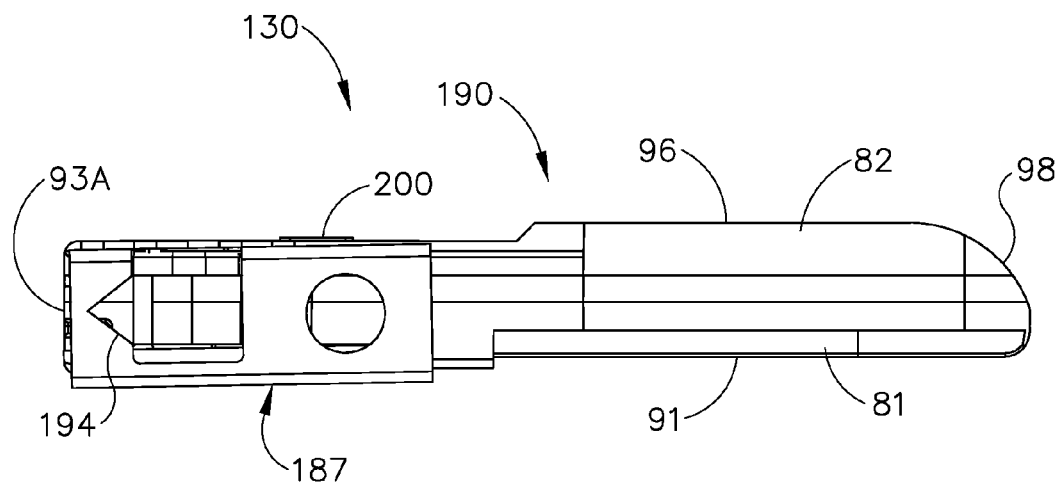
FIG. 9 depicts a right elevational view of the cartridge of FIG. 7.
Figure 10:
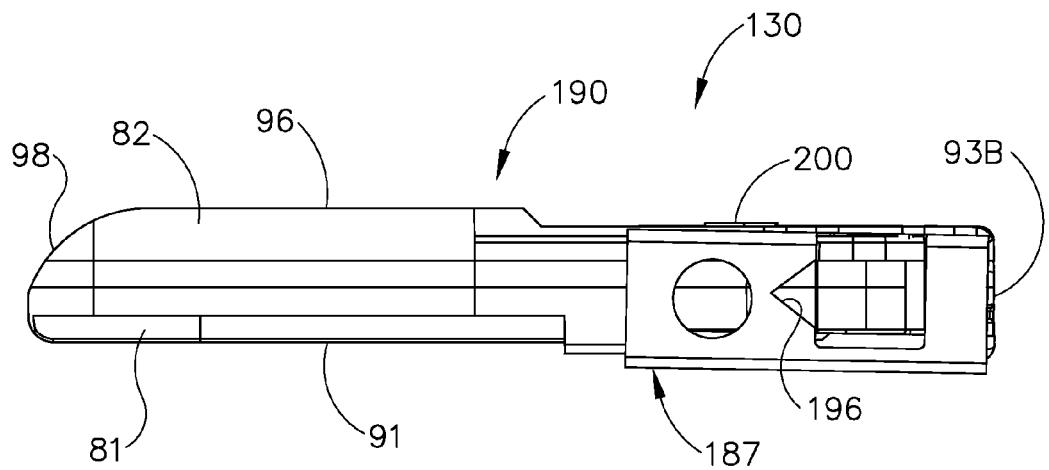
FIG. 10 depicts a left elevational view of the cartridge of FIG. 7.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (75) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C, when first input (12) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (95) and entrance port (97). Tissue interposed between arms (93A, 93B) will be pierced by leading end (71) of needle (70).

When first input (12) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first input (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) will follow needle (70) and be threaded through the pierced tissue.

When first input (12) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first input (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, now U.S. Pat. No. 9,357,998, issued Jun. 7, 2016 the disclosure of which is incorporated by reference herein; U.S. patent application Ser. No. 14/297,993, entitled "Jawed Receiver for Needle Cartridge," filed Jun. 6, 2014, now U.S. Pat. No. 9,474,522, issued Oct. 25, 2016 the disclosure of which is incorporated by reference herein; and U.S. patent application Ser. No. 14/298,038, entitled "Circular Needle Applier with Cleats," filed Jan. 30, 2015, now U.S. Pat. No. 9,375,212, issued Jun. 28, 2016 the disclosure of which is incorporated by reference herein. It should be understood that such details, explanations, examples, and alternative embodiments may be readily applied to the above-described instrument (10) and subcomponents thereof.

II. Exemplary Cartridge Features to Indicate Needle Motion

During operation of instrument (2), the operator may wish to visualize the orbital position of needle (70) and/or the direction in which needle (70) is traveling. However, needle (70) itself may either be in cartridge body (90) or in tissue at the particular stage where the operator wishes to visualize the orbital position of needle (70) and/or the direction in which needle (70) is traveling. Thus, cartridge body (90) and/or tissue may obscure the orbital position of needle (70) and/or the direction in which needle (70) is traveling. It may therefore be desirable to provide features that facilitate visualization of the orbital position of needle (70) and/or the direction in which needle (70) is traveling during operation of instrument, even when needle (70) is obscured by cartridge body (90) and/or tissue. By way of example only, exit arm (93A) may include a sticker, be painted, be colored, or otherwise be marked to visually indicate that exit arm (93A) is the arm (93A, 93B) from which leading end (71) of needle (70) will exit. Several additional examples of such features are described in greater detail below, while other examples will be apparent to those of ordinary skill in the art in view of the teachings herein.

A. Exemplary Cartridge with Needle Motion Indicator Arrows

FIGS. 7-10 show an exemplary alternative cartridge body (190) of an exemplary alternative needle applier cartridge (130). Needle applier cartridge (130) of the present example is configured to be substantially similar to needle cartridge (30) discussed above, except needle applier cartridge (130) includes features that indicate to an operator in which angular direction the needle is traveling, as discussed in more detail below. Similar to needle applier cartridge (30), needle applier cartridge (130) is configured to be connected to the distal end (22) of shaft (20) via cartridge receiving assembly (50). It should therefore be understood that cartridge (130) may be readily used with instrument (2).

Needle applier cartridge (130) is operable to rotate a curved needle (e.g. like needle (70)) in a circular orbital path, enabling a surgeon to selectively apply sutures. In some alternative versions, needle applier cartridge (130) is integral with shaft (20) and handle assembly (10) as a unitary disposable instrument intended for a single surgical procedure. Needle applier cartridge (130) may also be integral with shaft (20) and handle assembly (10) as a reusable instrument. Optionally, as illustrated here, needle applier cartridge (130) may be provided in disposable cartridge body (190), and shaft (20) includes cartridge receiving assembly (50) to releasably hold cartridge body (190) in a substantially similar manner that cartridge receiving assembly (50) holds cartridge body (50), as discussed above.

Still referring to FIGS. 7-10, cartridge body (190) includes many features that are substantially similar or identical to those of cartridge body (90). Therefore, such features are labeled with the same reference numerals without further discussion below. Cartridge body (190) of the present example includes a cage (187) slides over bodies (81, 82) and needle cover (83) to attach needle cover (83) against lower body (81). As shown, cage (187) includes at least one indicator that is configured to indicate to an operator the angular direction in which the needle is traveling. In the present example, the at least one indicator comprises a plurality of arrows (192, 194, 196) cut out of the body of cage (187) such that arrows (192, 194, 196) comprise arrow shaped apertures. In some examples, rather than being cutouts, any or all of arrows (192, 194, 196) may be configured in a different manner. For example, in some examples, any or all of arrows (192, 194, 196) may be formed as a surface deformation, texture, or printing on cage (187), such as a stamping, etching, pad printing, etc. Moreover, in some examples, any or all of arrows (192, 194, 196) may be separate components that are coupled or otherwise fixed to cage (187) by methods that will be apparent to persons having skill in the art in view of the teachings herein.

As shown, arrow (192) is on a side (198) of cage (187) that faces the same direction as lower face (91) of cartridge body (190). Arrow (192) is oriented to indicate that the needle will exit arm (93A) and enter arm (93B) during actuation of cartridge (130). Arrow (194) is adjacent to arm (93A) and is oriented to indicate that the needle will exit arm (93A) during actuation of cartridge (130). Arrow (196) is adjacent to arm (93B) and is oriented to indicate that the needle will enter arm (93B) during actuation of cartridge (130).

Cartridge body (190) includes an additional indicator which, in the example shown is an additional arrow (200) on upper face (96) of cartridge body (190). In the example shown, arrow (200) is pad printed onto upper face (96). However, in some examples, arrow (200) may be formed as a surface deformation, texture, or another form of printing on upper face (96), such as a stamping, etching, etc. Moreover, in some examples, arrow (200) may be a separate component that is coupled or otherwise fixed to cage upper face (96) by methods that will be apparent to persons having skill in the art in view of the teachings herein. Arrow (200) is oriented to indicate that the needle will exit arm (93A) and enter arm (93B) during actuation of cartridge (130).

In the present example, the locations of arrows (192, 194, 196, 200) enable an operator to determine the direction of needle travel when viewing cartridge (130) from various viewing angles. The operator only needs to have one arrow (192, 194, 196, 200) within the operator's field of view in order to determine the direction of needle travel, and having four arrows (192, 194, 196, 200) at the present locations may provide a high likelihood that at least one arrow (192, 194, 196, 200) is within the operator's field of view at any given stage of operation.

It should be understood that any of arrows (192, 194, 196, 200) may be located in different positions relative to cartridge body (190) as shown. Suitable other locations and configurations for arrows (192, 194, 196, 200) will be apparent to persons skilled in the art in view of the teachings herein. As will also be apparent to persons skilled in the art, because arrows (192, 194, 196, 200) are configured to correspond to the angular direction of needle movement, the configuration of arrows (192, 194, 196, 200) may be different depending on the configuration of needle movement discussed above. Moreover, while in the example shown the at least one indicator comprises arrows (192, 194, 196, 200), one or more of arrows (192, 194, 196, 200) may be omitted, or additional indicators (e.g., additional arrows) may be provided. In some examples, the at least one indicator need not comprise arrows. In such examples, the at least one indicator may be other features that are configured to indicate the direction of angular movement of the needle.

B. Exemplary Cartridge with Windows to View Needle Motion

FIGS. 11A-11D show an exemplary alternative cartridge body (290) of an exemplary alternative needle applier cartridge (230). Needle applier cartridge (230) of the present example is configured to be substantially similar to needle cartridge (30) discussed above, except that needle applier cartridge (130) includes features that indicate to an operator in which angular direction the needle is traveling, as discussed in more detail below. Similar to needle applier cartridge (30, 130), needle applier cartridge (230) is configured to be connected to the distal end (22) of shaft (20) via cartridge receiving assembly (50). It should therefore be understood that cartridge (230) may be readily used with instrument (2).

Needle applier cartridge (230) is operable to rotate a curved needle (70) in a circular orbital path, enabling a surgeon to selectively apply sutures. In some alternative versions, needle applier cartridge (230) is integral with shaft (20) and handle assembly (10) as a unitary disposable instrument intended for a single surgical procedure. Needle applier cartridge (230) may also be integral with shaft (20) and handle assembly (10) as a reusable instrument. Optionally, as illustrated here, needle applier cartridge (230) may be provided in disposable cartridge body (290) and shaft (20) includes cartridge receiving assembly (50) to releasably hold cartridge body (290), in a substantially similar manner that cartridge receiving assembly (50) holds cartridge body (50), as discussed above.

In the present example, still referring to FIGS. 11A-11D, cartridge body (290) includes many features that are substantially similar or identical to those of cartridge body (90). Therefore, such features are labeled with the same reference numerals without further discussion below. As shown, cartridge body (290) includes an upper body (282) and a lower body (not shown), that are substantially similar to upper and lower bodies (82, 81) of cartridge body (90), such that components like needle (70), needle driver (e.g. needle driver (86)), a rotary input (e.g., rotary input (94)), and a link (not shown) are captured between lower body and upper body (282). Lower body and upper body (282) may be attached to one another using a variety of known techniques, including welds, pins, adhesives, and the like to form cartridge body (290).

As shown in FIGS. 11A-D, upper body (282) includes a plurality of apertures or windows (284) that allow an operator to visualize an orbital position and/or a direction of motion of needle (70) during its actuation stroke. As shown, windows (284) follow the curvature of a needle track, such as needle track (84). In the present example, windows (284) include a shape that includes two opposing curved edges and two opposing straight edges. However, in other examples, windows (284) may include other shapes. Moreover, as shown, there are seven windows (284). However, in other examples, there may be more or less than seven windows (284), such as six or less, or eight or more. In the present example, windows (284) are shown to be only present on upper body (282). In other examples, there may be additional windows (284) or other features present on the lower body that allow an operator to view the orbital position of needle (70) when cartridge body (290) is oriented in a manner where, for example, windows (284) are out of the field of view of the operator. Moreover, windows (284) may be included on the example shown in FIGS. 7-10. Similarly, any or all of arrows (192, 194, 196, 200), or other indicators may be included on the example shown in FIGS. 11A-1D.

Figure 11A:
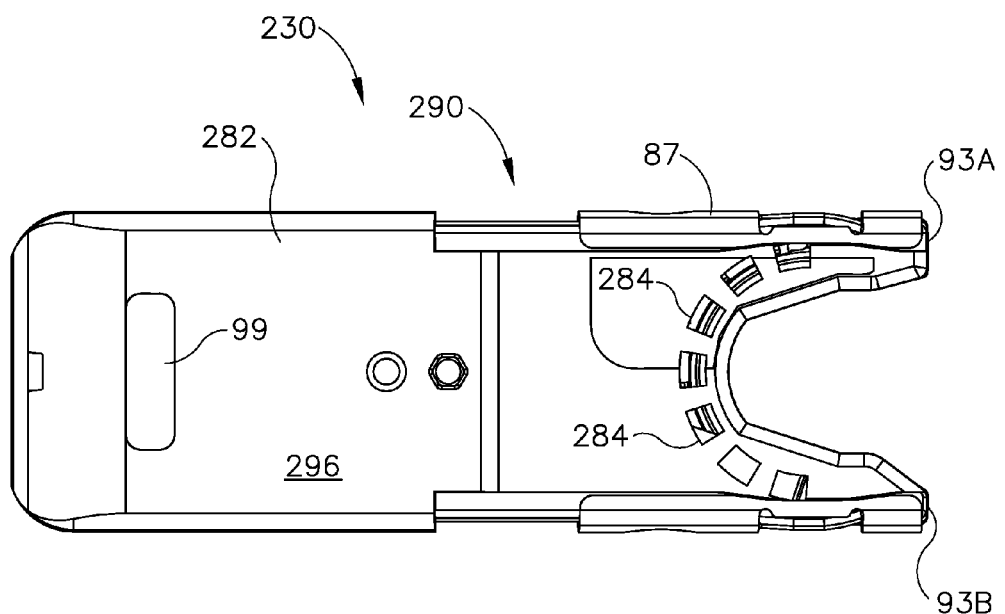
FIG. 11A depicts a top plan view of another exemplary alternative cartridge configured for receipt in the cartridge receiving assembly of FIG. 2A, with a needle in a first orbital position.
Figure 11B:
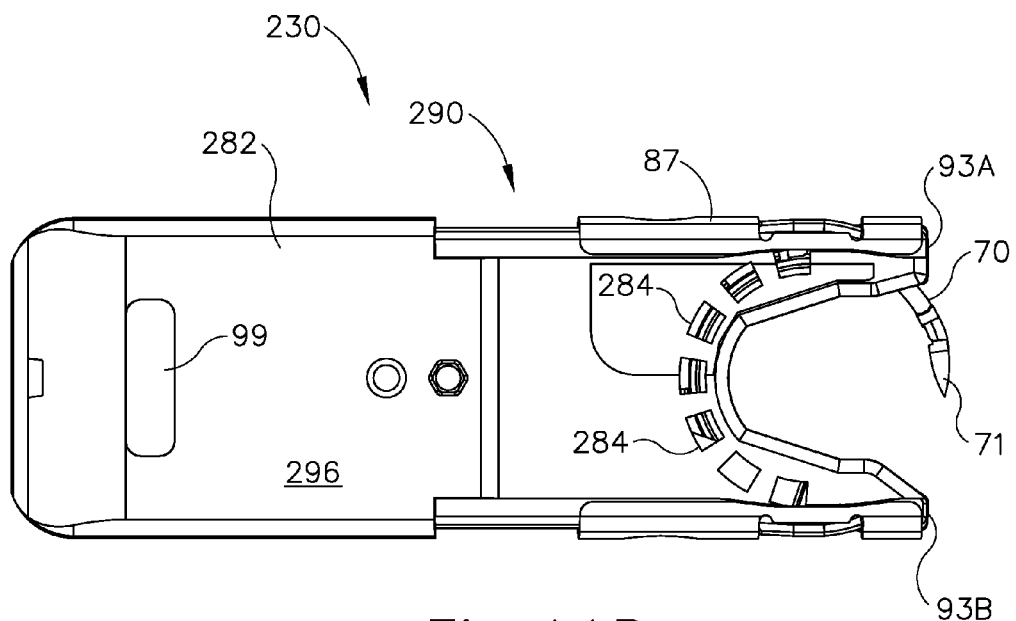
FIG. 11B depicts a top plan view of the cartridge of FIG. 11A, with the needle in a second orbital position.
Figure 11C:
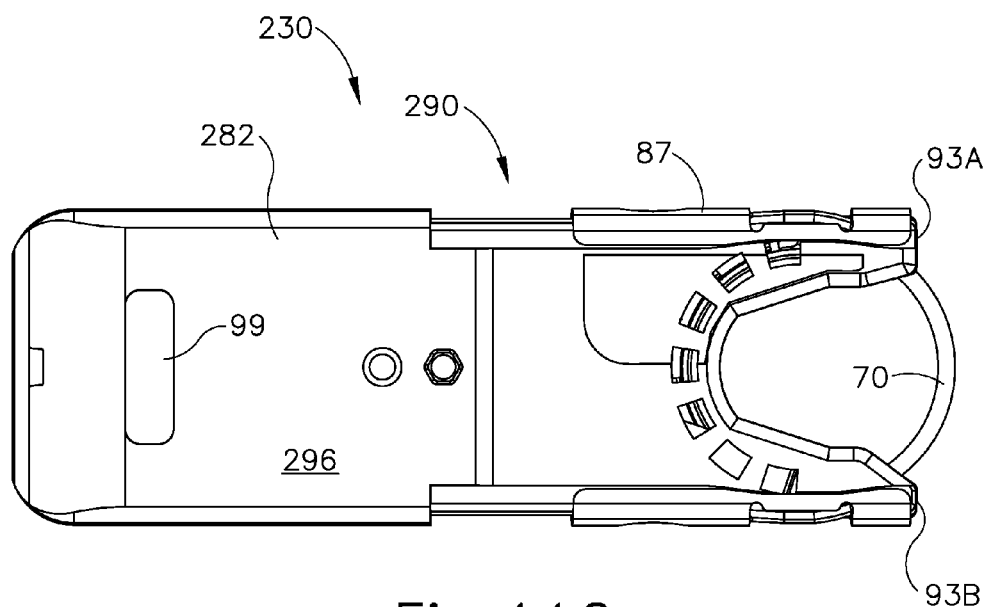
FIG. 11C depicts a top plan view of the cartridge of FIG. 11A, with the needle in a third orbital position.
Figure 11D:
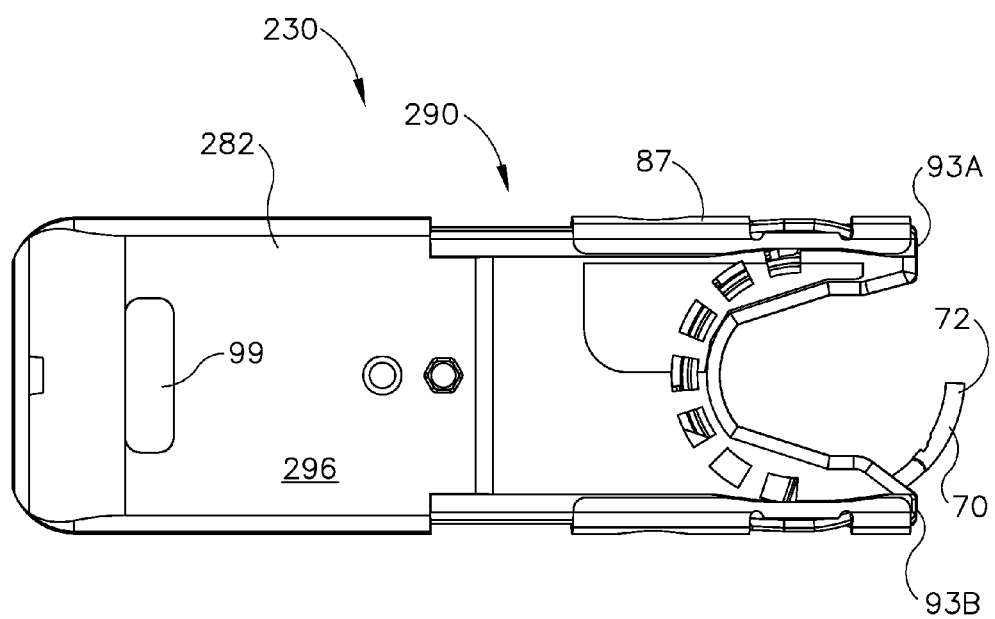
FIG. 11D depicts a top plan view of the cartridge of FIG. 11A, with the needle in a fourth orbital position.

FIGS. 11A-11D show a partial orbital range of motion of needle (70) through cartridge body (290). It will be understood that suture (73) has been omitted from FIGS. 11A-11D for clarity. It will be understood that the position of needle (70) as shown in FIG. 11A corresponds with the state of needle driver (86) shown in FIG. 5A. The position of needle (70) shown in FIG. 11B corresponds with the state of needle driver (86) shown in FIG. 5B. Needle (70) in FIG. 11C is shown to be in an orbital position that corresponds with the state of needle driver (86) shown in FIG. 5A. The position of needle (70) shown in FIG. 11D corresponds with the state of needle driver in FIG. 5B.

Due to the presence of windows (284), the operator may visualize the position of the needle (70) at all of the stages of actuation shown in FIGS. 11A-11D. For example, the absence of needle (70) showing through windows (284) may indicate that needle (70) is in a position such that it is traveling through tissue. Similarly, the presence of needle (70) showing through windows (284) may indicate that at least a portion of needle is has not exited from exit port (95) and is still present in needle track (84). Windows (284) may also enable the operator to visualize the position of leading end (71) of needle (70) or trailing end (72) of needle (70) in cartridge body (290), which may provide more precise feedback on the particular orbital position of needle (70) at a given stage of operation. Of course, it will be understood that the operator may visualize the absence or presence of at least a portion of needle (70) through windows (284) in any of the positions shown in FIGS. 11A-11D, or in positions that are different than those shown in FIGS. 11A-11D. The sequence may be repeated as needed by the surgeon to achieve the desired suturing task.

FIGS. 12-14B show an exemplary alternative cartridge body (390) of an exemplary alternative needle applier cartridge (330). Needle applier cartridge (330) of the present example is configured to be substantially similar to needle cartridge (30, 130, 230) discussed above, except for the differences discussed below. Similar to needle applier cartridge (30, 130, 230), needle applier cartridge (330) is configured to be connected to the distal end (22) of shaft (20) via cartridge receiving assembly (50). It should therefore be understood that cartridge (330) may be readily used with instrument (2).

Needle applier cartridge (330) is operable to rotate a curved needle (70) in a circular orbital path, enabling a surgeon to selectively apply sutures. In some alternative versions, needle applier cartridge (330) is integral with shaft (20) and handle assembly (10) as a unitary disposable instrument intended for a single surgical procedure. Needle applier cartridge (330) may also be integral with shaft (20) and handle assembly (10) as a reusable instrument. Optionally, as illustrated here, needle applier cartridge (330) may be provided in disposable cartridge body (390) and shaft (20) includes cartridge receiving assembly (50) to releasably hold cartridge body (390), in a substantially similar manner that cartridge receiving assembly (50) holds cartridge body (50), as discussed above.

As shown, cartridge body (390) includes an upper body (382) and a lower body (381) (FIG. 13), that are substantially similar to upper and lower bodies (82, 81) of cartridge body (90), such that components like needle (70), needle driver (398), a rotary input (e.g., rotary input (94)), and a link (385) are captured between lower body (381) and upper body (382). Bodies (381, 382) may be attached to one another using a variety of known techniques, including welds, pins, adhesives, and the like to form cartridge body (390). It will be understood that suture (73) has been omitted from FIGS. 12A-14B, though suture (73) would be secured to trailing end (72) of needle (70).

Still referring to FIGS. 12A-14B, cartridge body (390) is configured to operate in as substantially similar manner to cartridge body (90, 190, 290), except for the differences discussed below. Particularly, cartridge body (390) includes windows (384a, 384b) in upper body (382) that enable the operator to visualize the orbital position of needle (70) in needle track (384). Windows (384a, 384b) also enable the operator to visualize the direction in which needle (70) is traveling. Windows (384a) are positioned radially inwardly relative to windows (384b). Windows (384a) are in the form of arrows pointing along an orbital path toward arm (93a). Windows (384b) are in the form of arrows pointing along an orbital path toward arm (93b).

Cartridge (390) further comprises an indicator member (392) extending upwardly from needle driver (398) and an indicator cam projection (394) extending downwardly from an inner wall (396) of upper body (382). Indicator member (392), is visible through windows (384a, 384b) to enable an operator to determine the direction in which needle driver (398) is traveling. Indicator member (392) is joined with needle driver (398) by a living hinge and defines a "T" shape. Indicator member (392) comprises a first portion (400) that is flexible and a second portion (402) that is transverse to the first portion (400). The upper side of second portion (402) is colored to enhance the visibility of second portion through windows (384a, 384b) during actuation of cartridge (330).

Figure 13:
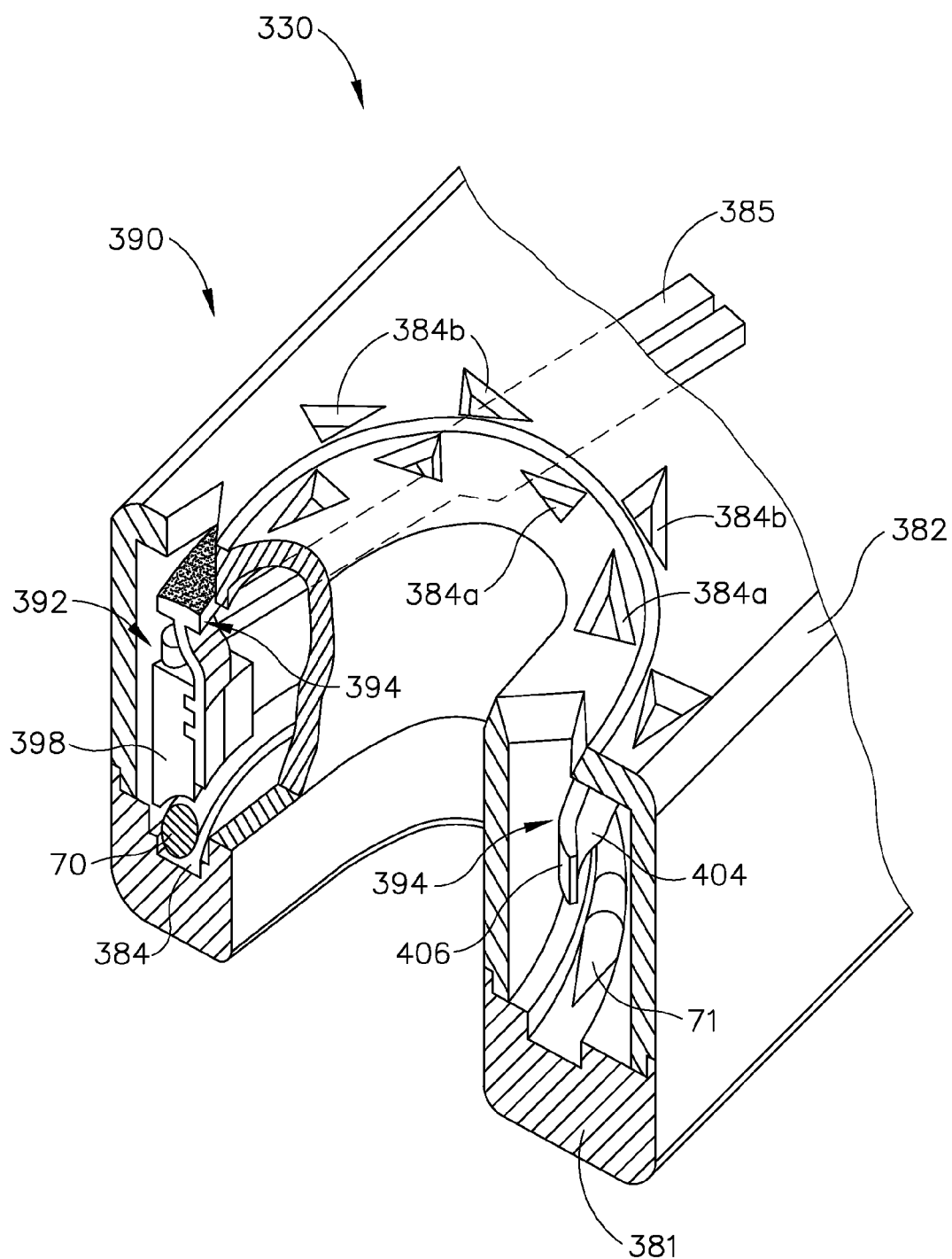
FIG. 13 depicts a perspective view of the distal end of the cartridge of FIG. 12, with a portion of the distal end shown in cross-section.
Figure 14A:
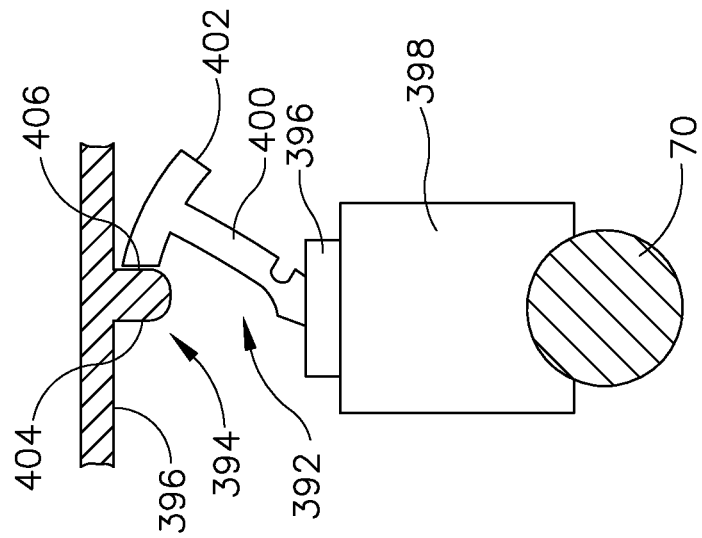
FIG. 14A depicts a cross-sectional view of a portion of the cartridge of FIG. 12, showing a needle position indicator in a first position to indicate orbital movement of the needle in a first angular direction.
Figure 14B:
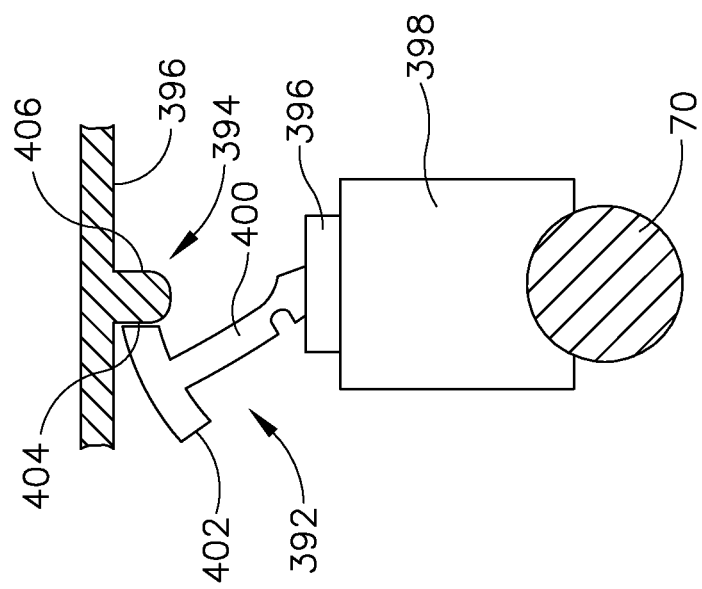
FIG. 14B depicts a cross-sectional view of a portion of the cartridge of FIG. 12, showing a needle position indicator in a second position to indicate orbital movement of the needle in a second angular direction.

As link (385) and needle driver (398) move from the state shown in FIGS. 12 and 13 (which corresponds to the state of link (85) shown in FIG. 5A), indicator member (392) rides along an outer surface (404) of indicator cam projection (394), as seen best in FIG. 14A. Thus, indicator member (392) is visible through windows (384b) as it travels along outer surface (404). When link (385) and needle driver (398) reach a state that corresponds with the state of link (85) shown FIG. 5C, indicator member (392) travels beyond an end of indicator cam projection (394) and flexes over to an inner surface (406) of indicator cam projection (394). FIG. 14B shows the position of the flex indicator riding against inner surface (406) of indicator cam projection (394) just prior to link (385) and needle driver (398) again reaching the state shown in FIGS. 12 and 13 (which corresponds to the state of link (85) shown in FIG. 5A). Once link (385) and needle driver (398) again reaches the state shown in FIGS. 12 and 13, flex indicator member (392) reaches the other end of indicator cam projection (394) and flexes back over to outer surface (404). At this point, needle (70) is in an orbital position where link (385) has been actuated once and needle (70) has only traveled angularly 180° after a single actuation of first input (12). The operator may actuate first input (12) another time, thereby causing the link (385) and needle driver (398) to actuate once again as discussed above, and causing needle (70) to travel angularly an additional 180°.

As shown, as indicator member (392) rides along outer surface (404) of indicator cam projection (394), indicator member (392) is visible through windows (384b). Similarly, as indicator member (392) rides along inner surface (406) of indicator cam projection (394), indicator member (392) is visible through windows (384a). Moreover, as best seen in FIG. 12, needle (70) is visible through windows (384a). For example, the absence of needle (70) showing through windows (284) may indicate that needle (70) is in a position such that needle (70) is traveling through tissue. Similarly, the presence of needle (70) showing through windows (384a, 384b) may indicate that at least a portion of needle is has not exited from exit port (95) and is still present in needle track (84). Windows (384a) may also enable the operator to visualize the position of leading end (71) of needle (70) or trailing end (72) of needle (70) in cartridge body (290), which may provide more precise feedback on the particular orbital position of needle (70) at a given stage of operation. Of course, it will be understood that the operator may visualize the absence or presence of at least a portion of needle (70) through windows (284) in any of the positions of needle (70), such as positions that are similar to those shown in FIGS. FIGS. 11A-D.

C. Exemplary Cartridge with Needle Motion Indicator Pin in Slot

Figure 15:
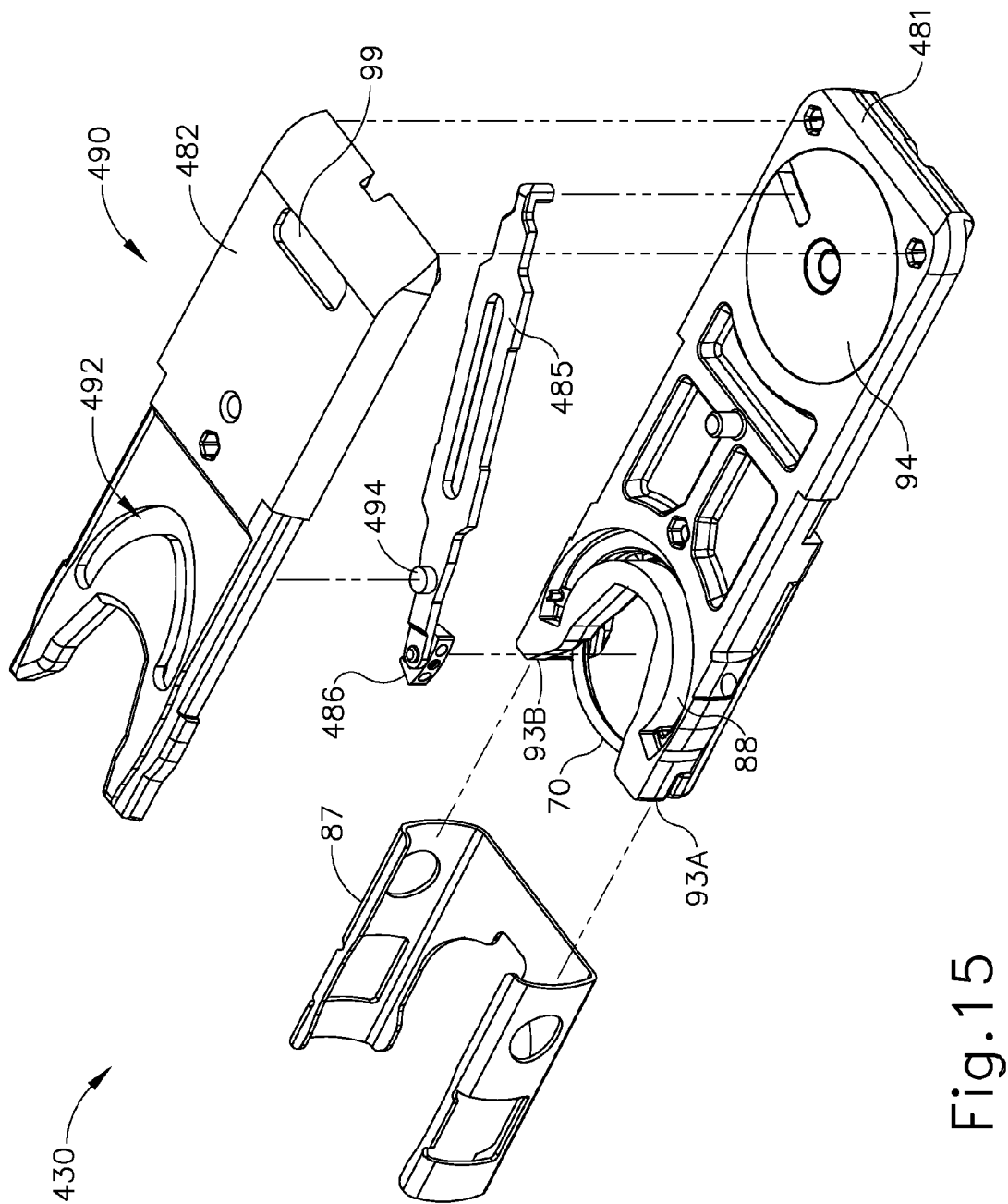
FIG. 15 depicts an exploded view of another exemplary alternative cartridge configured for receipt in the cartridge receiving assembly of FIG. 2A.
Figure 16A:
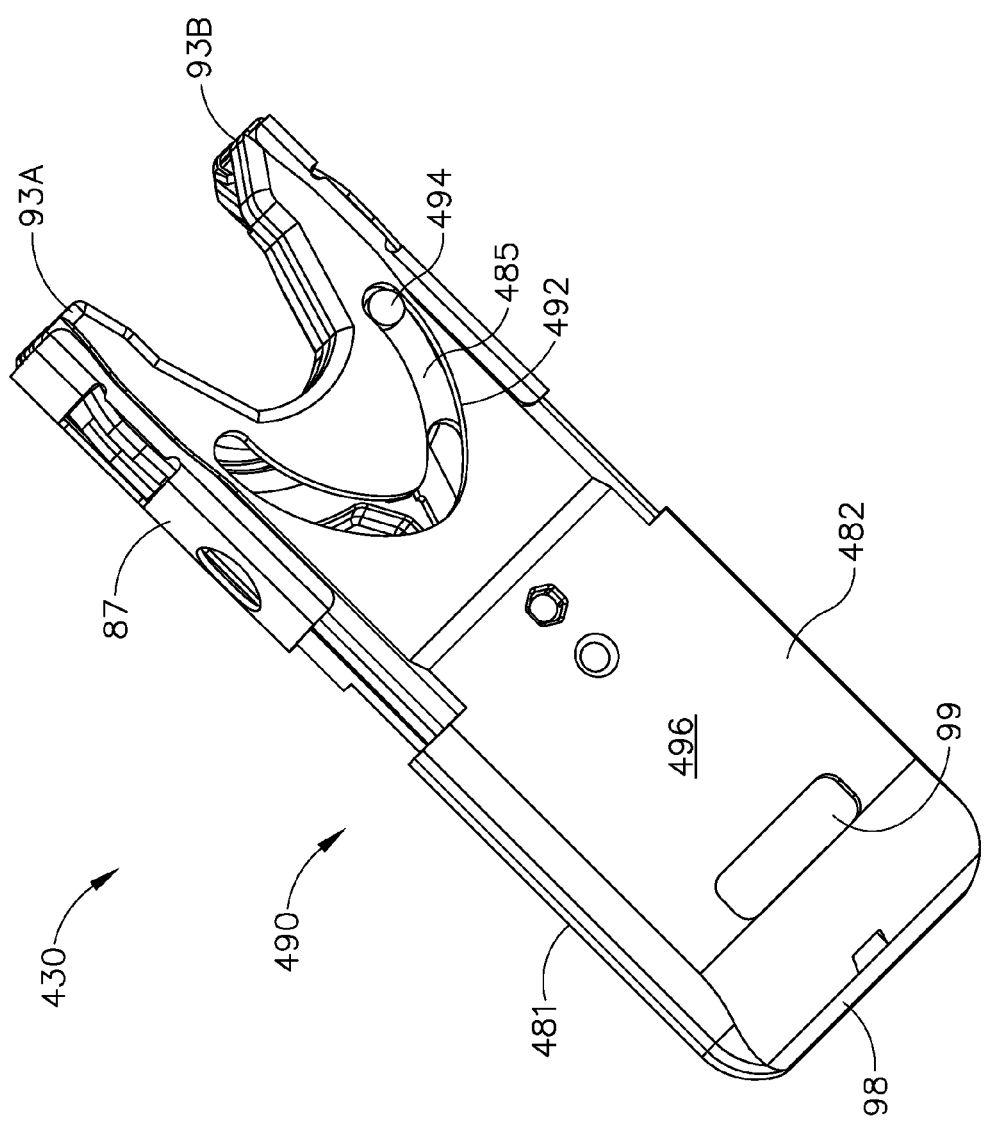
FIG. 16A depicts a perspective view of the cartridge of FIG. 15, with a needle drive link in a first position and a needle in a first orbital position.
Figure 16B:
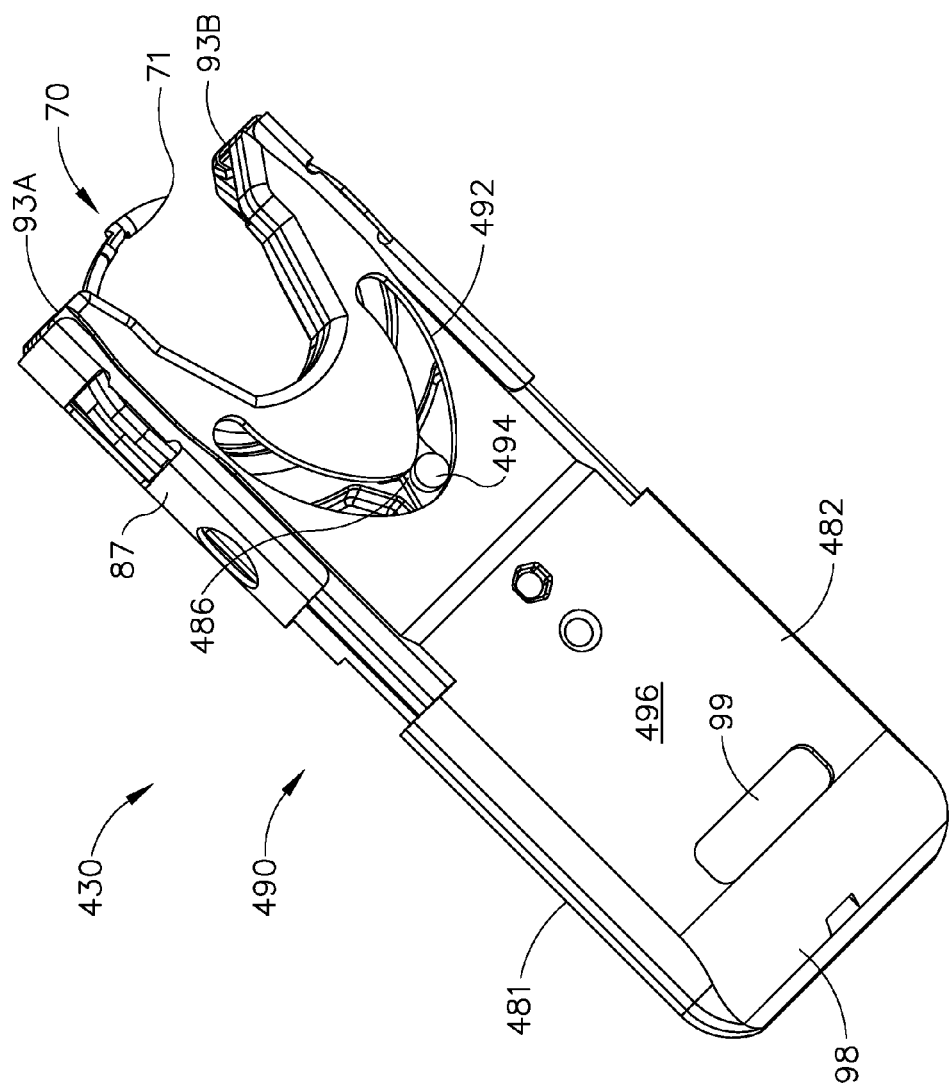
FIG. 16B depicts a perspective view of the cartridge of FIG. 15, with the needle drive link in a second position and the needle in a second orbital position.
Figure 16C:
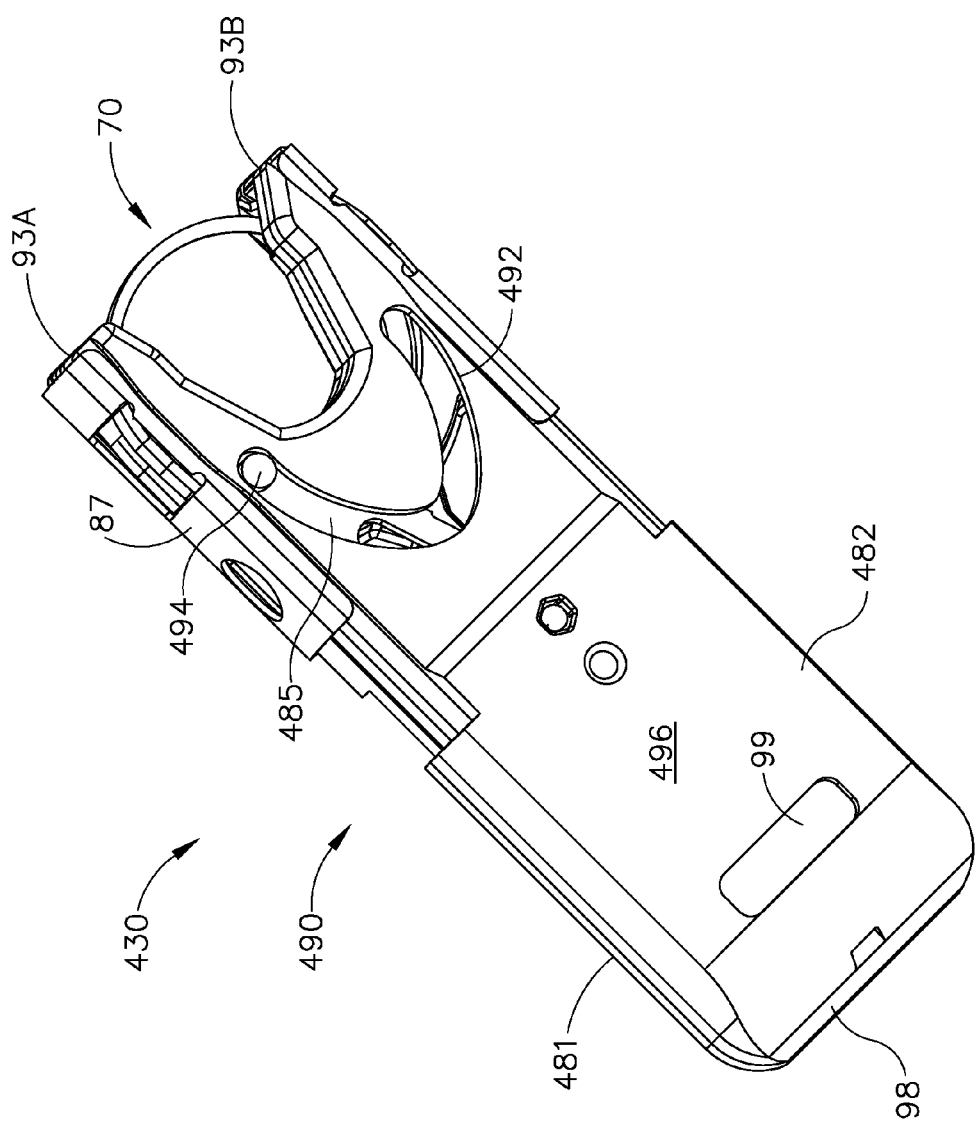
FIG. 16C depicts a perspective view of the cartridge of FIG. 15, with the needle drive link in a third position and the needle in a third orbital position.
Figure 16D:
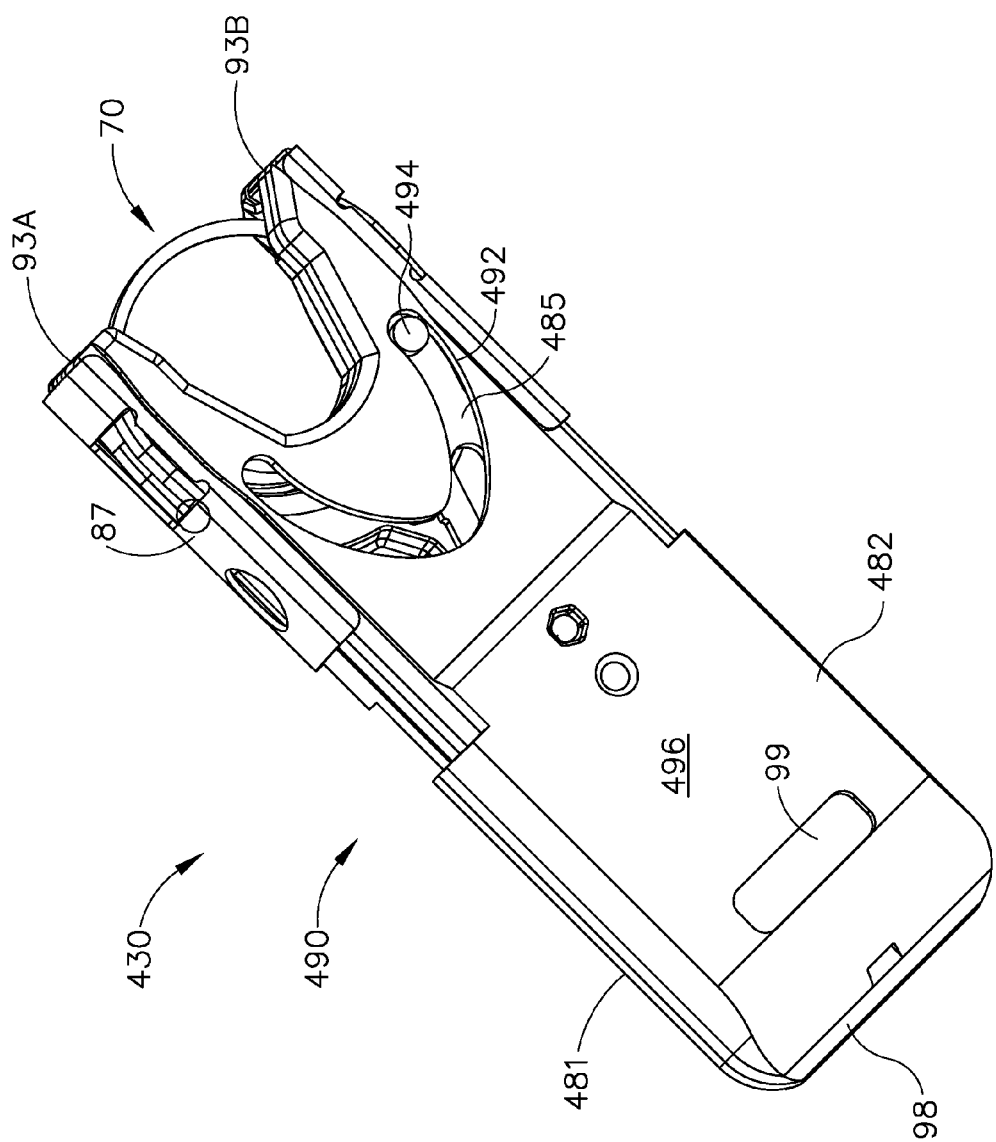
FIG. 16D depicts a perspective view of the cartridge of FIG. 15, with the needle drive link in the first position and the needle in the third orbital position.
Figure 16E:
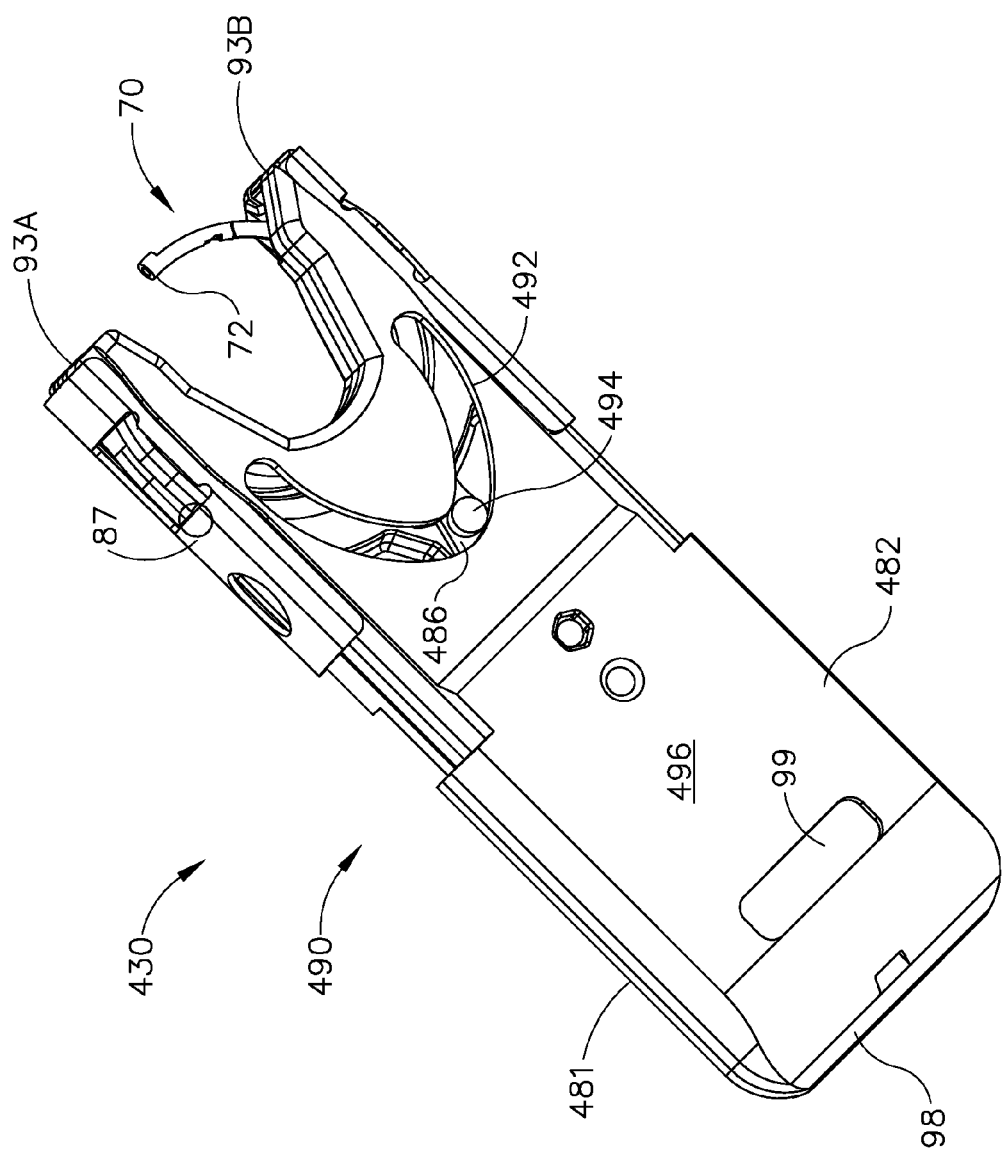
FIG. 16E depicts a perspective view of the cartridge of FIG. 15, with the needle drive link in the second position and the needle in a fourth orbital position.
Figure 16F:
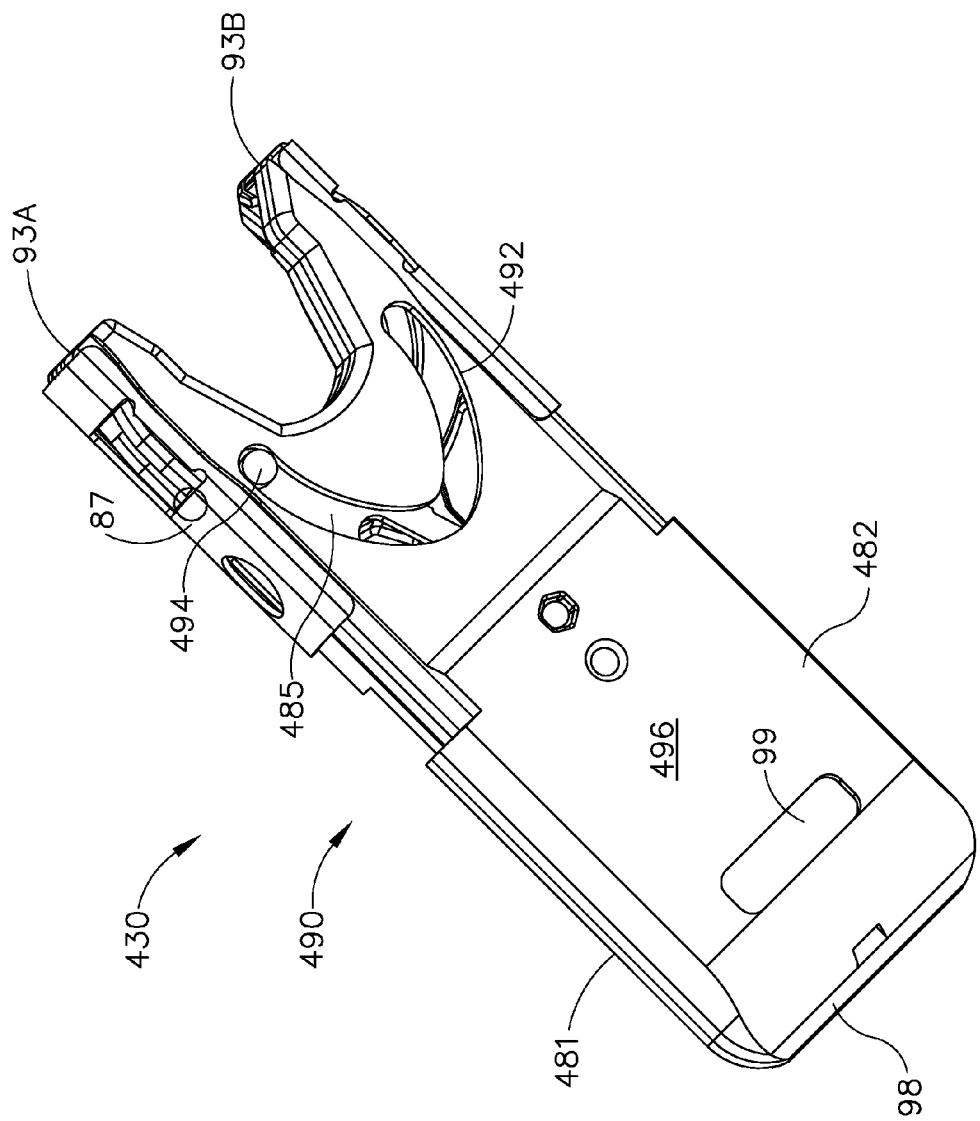
FIG. 16F depicts a perspective view of the cartridge of FIG. 15, with the needle drive link in the third position and the needle in the first orbital position.

FIGS. 15-16F show an exemplary alternative cartridge body (490) of an exemplary alternative needle applier cartridge (430). Needle applier cartridge (430) of the present example is configured to be substantially similar to needle cartridge (30) discussed above, except that needle applier cartridge (430) includes features that indicate to an operator in which angular direction the needle is traveling, as discussed in more detail below. Similar to needle applier cartridge (30, 130, 230, 330), needle applier cartridge (430) is configured to be connected to the distal end (22) of shaft (20) via cartridge receiving assembly (50). It should therefore be understood that cartridge (430) may be readily used with instrument (2).

Needle applier cartridge (430) is operable to rotate a curved needle (70) in a circular orbital path, enabling a surgeon to selectively apply sutures. In some alternative versions, needle applier cartridge (430) is integral with shaft (20) and handle assembly (10) as a unitary disposable instrument intended for a single surgical procedure. Needle applier cartridge (430) may also be integral with shaft (20) and handle assembly (10) as a reusable instrument. Optionally, as illustrated here, needle applier cartridge (430) may be provided in disposable cartridge body (490) and shaft (20) includes cartridge receiving assembly (50) to releasably hold cartridge body (490), in a substantially similar manner that cartridge receiving assembly (50) holds cartridge body (50), as discussed above.

Cartridge body (490) includes many features that are substantially similar or identical to those of cartridge body (90). Therefore, such features are labeled with the same reference numerals without further discussion below. As shown, cartridge body (490) includes an upper body (482) and a lower body (481) that are substantially similar to upper and lower bodies (82, 81) of cartridge body (90), such that components like a needle (70), a needle driver (486), a rotary input (94), and a link (485) are captured between lower body (481) and upper body (482). Bodies (481, 482) may be attached to one another using a variety of known techniques, including welds, pins, adhesives, and the like to form cartridge body (490).

Upper body (482) includes at least one indicator that is configured to indicate to an operator the angular direction in which needle (70) is traveling and/or the position of needle (70) relative to needle track (84), for example. In the present example, as shown in FIGS. 15-16F, the indicator comprises a track in the form of an elongate, curved slot (492) that is formed in upper face (496) of upper body (482), and an indicator pin (494) that rides along slot (492). As best seen in FIG. 15, pin (494) projects transversely from link (485), and is located at a position that is proximal to the distal end where link (485) is coupled with needle driver (486). Pin (494) rides along slot (492) as link (485) and needle driver (486) move in response to actuation of an input, such as first input (12). Slot (492) thus defines a path that is followed by at least a portion of link (485) as cartridge (430) is actuated. As can be clearly seen in FIGS. 15-16F, the indicator track in the form of curved slot (492) is nonaligned with the circular/orbital path of needle (70).

FIGS. 16A-16F illustrate an example of two successive drive strokes of the drive assembly in cartridge body (490) for driving needle (70) in a circular, orbital path. It should be understood that suture (73) is omitted from FIGS. 16A-16F. It will be also be understood that needle (70) is driven via rotary input (94), link (485) (similar to link (85)), and needle driver (486) (similar to needle driver (86)) in the same manner as described with respect to the components shown in FIGS. 5A-5C. Particularly, needle driver (486) rides in carrier track (88) (FIGS. 5A-5C) and extends into needle track (e.g., needle track (84)) to engage and drive needle (70). Link (485) connects rotary input (94) to needle driver (486).

FIG. 16A shows link (485), and thus pin (494), positioned at one end of its stroke in slot (492), in a position that corresponds with the position of link (85) shown in FIG. 5A. As shown in FIG. 16B, counterclockwise rotation of rotary input (94) will translate needle driver (486) clockwise along carrier track, thereby causing translation of pin (494) clockwise along slot (492), and also driving needle (70) clockwise. The position of needle driver (486) and link (485) shown in FIG. 16B corresponds with the position of needle driver (86) and link (85) shown in FIG. 5B. As shown in FIG. 16C, continued counterclockwise rotation of rotary input (94) will continue to translate needle driver (486) in a clockwise manner along slot (492) to the position shown in FIG. 16C, and thereby drive needle (70) clockwise until it reaches the other end of its stroke in carrier track (88), as also shown in FIG. 16C. In this example, the drive stroke rotates the needle (70) in its circular path along an angular range of about 180 degrees.

For the return stroke, the sequence can be reversed by rotating rotary input (94) clockwise, which will translate needle driver (486) counterclockwise in carrier track (88). Needle driver (486) is disengaged from needle (70) during the return stroke until needle driver (486) reaches the end of the return stroke, as shown in FIG. 16D. Needle driver (486) will re-engage needle (70) upon completing the return stroke. Then, as shown in FIG. 16E, counterclockwise rotation of rotary input (94) will translate needle driver (486) clockwise along carrier track (88), thereby causing translation of pin (494) clockwise along slot (492), and also driving needle (70) clockwise. The position of needle driver (486) and link (485) shown in FIG. 16E corresponds with the position of needle driver (86) and link (85) shown in FIG. 5B. As shown in FIG. 16F, continued counterclockwise rotation of rotary input (94) will continue to translate needle driver (486) in a clockwise manner along slot (492) to the position shown in FIG. 16F, and thereby drive needle (70) clockwise until it reaches the other end of its stroke in carrier track (88), as also shown in FIG. 16F. Thus, a sequence of drive and return strokes drives the needle (70) in a circular, orbital path. Due to the presence of slot (492), an operator may visualize the position of pin (494), and thus the orbital position of needle driver (486), link (485), and thus needle (70). Observing the movement of pin (494) also allows the operator to visualize the direction of angular movement of needle (70).

It will be understood that even though certain indicators are shown to be in embodied in separate examples, any or all of the indicators discussed herein may be included in some examples. For example, any or all of arrows (192, 194, 196, 200) may also be included in cartridge bodies (290, 390, 490); any or all of windows (284) may be included in cartridge bodies (190, 390, 490); any or all of windows (384a, 384b) may be included in cartridge bodies (190, 290, 490), and slot (492) and pin (494) may be included in cartridge bodies (190, 290, 390). Various suitable combinations of the teachings herein will be apparent to those of ordinary skill in the art.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument comprising: (a) a body; (b) a user input feature; (c) an elongate shaft extending distally from the body along a longitudinal axis; (d) a needle applier coupled to the elongate shaft, wherein the needle applier further comprises: (i) a needle, (ii) a drive assembly coupled to the needle, wherein the drive assembly is configured to drive the needle about a rotation axis that is transverse to the longitudinal axis, in response to an actuation of the user input feature, and (iii) a housing containing the needle and the drive assembly, wherein the housing presents at least one indicator, wherein the at least one indicator is positioned and configured to visually to indicate at least one of the following: (A) a position of the needle relative to the housing, or (B) a direction of rotation of the needle relative to the housing.

EXAMPLE 2

The surgical instrument according to Example 1, wherein the at least one indicator comprises an arrow.

EXAMPLE 3

The surgical instrument according to Example 2, wherein the arrow comprises an arrow shaped aperture.

EXAMPLE 4

The surgical instrument according to any one or more of Examples 2 through 3, wherein the arrow comprises a print on the housing.

EXAMPLE 5

The surgical instrument according to any one or more of Examples 2 through 4, wherein the needle applier further comprises opposing arms, wherein the arrow is disposed on at least one of the opposing arms.

EXAMPLE 6

The surgical instrument according to any one or more of Examples 1 through 5, wherein the at least one indicator comprises a plurality of apertures in the housing.

EXAMPLE 7

The surgical instrument according to Example 6, wherein the needle applier comprises a needle track along which the needle is configured to travel, wherein at least some of the plurality of apertures are coincident with the needle track to enable an operator to view the absence or presence of at least a portion of the needle in the needle track.

EXAMPLE 8

The surgical instrument according to Example 7, wherein the needle applier further comprises: (A) a projection opposing the needle track, wherein the projection extends from an inner portion of the housing, and (B) an indicator member coupled to the drive assembly, wherein the indicator member is configured to rotate in response to operation of the drive assembly, wherein the indicator member is configured to cam against the projection as the indicator member rotates.

EXAMPLE 9

The surgical instrument according to Example 8, wherein the indicator member is configured to pivot as the indicator member cams against the projection.

EXAMPLE 10

The surgical instrument according to any one or more of Examples 8 through 9, wherein the indicator member is configured to be visible through at least one of the plurality of apertures.

EXAMPLE 11

The surgical instrument according to Example 10, wherein the projection includes a radially inner portion and a radially outer portion, wherein the indicator member is configured to cam against one of the radially inner and outer portions as the indicator member rotates in a first direction, wherein the indicator member is configured to cam against the other of the radially inner and outer portions as the indicator member rotates in a first direction.

EXAMPLE 12

The surgical instrument according to Example 11, wherein the plurality of apertures includes a radially outward set of apertures and a radially inward set of apertures, wherein the indicator member is configured to be visible through at least one of the radially outward set of apertures as the indicator member cams against the radially outer portion, wherein the indicator member is configured to be visible through at least one of the radially inward set of apertures as the indicator member cams against the radially inner portion.

EXAMPLE 13

The surgical instrument according to any one or more of Examples 1 through 12, wherein the at least one indicator comprises a slot in the housing, wherein at least a portion of the drive assembly is visible through the slot.

EXAMPLE 14

The surgical instrument according to Example 13, wherein the indicator further comprises a pin, wherein the pin is configured to ride along the slot in response to operation of the drive assembly.

EXAMPLE 15

The surgical instrument according to Example 14, wherein the drive assembly comprises a drive link, wherein the pin is operably coupled to the drive link.

EXAMPLE 16

A method for operating an instrument, wherein the instrument comprises: (a) a body comprising an input; (b) an elongate shaft extending from the body along a longitudinal axis; and (c) a needle applier coupled to the elongate shaft, the needle applier comprising: (i) a needle, (ii) a drive assembly coupled to the needle, wherein the drive assembly is configured to drive the needle along an orbital path about an axis that is transverse to the longitudinal axis, in response to an actuation of the input, and (iii) a housing containing the needle and the drive assembly, wherein the housing presents at least one indicator, wherein the at least one indicator is positioned to indicate a position of the needle relative to the housing or a direction of orbital travel of the needle; wherein the method comprises: (a) positioning the needle applier adjacent to tissue; (b) actuating the input, thereby activating the drive assembly to drive the needle through the tissue; and (c) observing the at least one indicator to determine a position of the needle relative to the housing or a direction of orbital travel of the needle.

EXAMPLE 17

The method according to Example 16, wherein the body comprises a handle assembly, wherein the input comprises a trigger.

EXAMPLE 18

The method according to any one or more of Examples 16 through 17, wherein the housing further comprises an aperture configured to view components internal to the housing.

EXAMPLE 19

The method according to any one or more of Examples 16 through 18, wherein observing the at least one indicator comprises observing a path of motion the at least one indicator as the drive assembly operates.

EXAMPLE 20

A needle applier cartridge configured to be coupled to a needle applying instrument, the needle applier cartridge comprising: (a) a needle; (b) a drive assembly coupled to the needle, wherein the drive assembly is configured drive the needle along an orbital path about a rotation axis; and (c) a housing containing the needle and the drive assembly, wherein the housing presents at least one indicator configured to enable an operator to visualize an orbital direction or position of the needle or a portion of the drive assembly relative to the housing.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
  (a) a body;
  (b) a user input feature;
  (c) an elongate shaft extending distally from the body along a longitudinal axis;
  (d) a needle applier coupled to the elongate shaft, wherein the needle applier cartridge further comprises:
    (i) a needle,
    (ii) a drive assembly coupled to the needle, wherein the drive assembly is configured to drive the needle along a circular path about a rotation axis that is transverse to the longitudinal axis, in response to an actuation of the user input feature, and
    (iii) a housing containing the needle and the drive assembly, wherein the housing presents at least one indicator, wherein the at least one indicator includes an indicator track that is nonaligned with the circular path of the needle, wherein the at least one indicator is positioned and configured to visually indicate at least one of the following:
      (A) a position of the needle relative to the housing, or
      (B) a direction of rotation of the needle relative to the housing; and wherein the drive assembly is configured to translate within the circular path during a drive stroke and a return stroke.

2. The surgical instrument according to claim 1, wherein the at least one indicator track comprises a slot in the housing, wherein at least a portion of the drive assembly is visible through the slot.

3. The surgical instrument according to claim 2, wherein the indicator further comprises a pin, wherein the pin is configured to ride along the slot in response to operation of the drive assembly.

4. The surgical instrument according to claim 3, wherein the drive assembly comprises a drive link, wherein the pin is operably coupled to the drive link.

5. A needle applier cartridge configured to be coupled to a needle applying instrument, the needle applier cartridge comprising:
  (a) a needle;
  (b) a drive assembly coupled to the needle, wherein the drive assembly is configured to drive the needle along an orbital path about a rotation axis, wherein the drive assembly is configured to translate within the orbital path during a drive stroke and a return stroke; and
  (c) a housing containing the needle and the drive assembly, wherein the housing presents at least one indicator configured to slidably receive the drive assembly to thereby enable an operator to visualize an orbital direction or position of a portion of the drive assembly relative to the housing, wherein the at least one indicator include an indicator track that is nonaligned with the orbital path of the needle;
  wherein the orbital direction or position of the portion of the drive assembly relative to the housing corresponds to the orbital direction or position of the needle relative to the rotation axis.

6. The surgical instrument of claim 1, wherein the needle applier cartridge is removably coupled to the elongate shaft such that the end effector is configured to be selectively attached to the elongate shaft.

* * * * *